(12) United States Patent
Tonks et al.

(10) Patent No.: US 11,660,306 B2
(45) Date of Patent: May 30, 2023

(54) TREATMENT OF RETT SYNDROME

(71) Applicant: Cold Spring Harbor Laboratory, Cold Spring Harbor, NY (US)

(72) Inventors: Nicholas Tonks, Cold Spring Harbor, NY (US); Navasona Krishnan, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 16/377,875

(22) Filed: Apr. 8, 2019

(65) Prior Publication Data
US 2019/0247408 A1 Aug. 15, 2019

Related U.S. Application Data

(62) Division of application No. 15/514,415, filed as application No. PCT/US2015/051594 on Sep. 23, 2015, now abandoned.

(60) Provisional application No. 62/185,214, filed on Jun. 26, 2015, provisional application No. 62/055,433, filed on Sep. 25, 2014.

(51) Int. Cl.
*A61K 31/662* (2006.01)
*C07F 9/38* (2006.01)
*C12Q 1/6883* (2018.01)

(52) U.S. Cl.
CPC .......... *A61K 31/662* (2013.01); *C07F 9/3808* (2013.01); *C12Q 1/6883* (2013.01); *C12Q 2600/156* (2013.01)

(58) Field of Classification Search
CPC ................ A61K 31/662; C12Q 1/6883; C12Q 2600/156
See application file for complete search history.

(56) References Cited

U.S. PATENT DOCUMENTS

| | | | |
|---|---|---|---|
| 6,709,817 B1 | 3/2004 | Zoghbi et al. | |
| 7,504,389 B2* | 3/2009 | Blaskovich | C07F 9/3808 514/114 |
| 7,829,737 B2 | 11/2010 | Blaskovich et al. | |
| 7,994,127 B2 | 8/2011 | Sur et al. | |
| 2004/0191926 A1 | 9/2004 | Zhang et al. | |
| 2009/0131374 A1 | 5/2009 | Blaskovich et al. | |
| 2012/0252009 A1 | 10/2012 | Feehery et al. | |
| 2013/0029366 A9 | 1/2013 | Tonks et al. | |
| 2015/0119327 A1* | 4/2015 | Muotri | A61K 31/4045 514/8.6 |

FOREIGN PATENT DOCUMENTS

JP 2008050263 A 3/2008

OTHER PUBLICATIONS

Keedy; downloaded https://doi.org/10.1101/218966; Nov. 13, 2017.*
Examination report No. 1 dated Apr. 26, 2019 issued in Australian Patent Application No. 2015320748.
Montalibet J et al: "Residues distant from the active site influence protein-tyrosine phosphatase 1B inhibitor binding", J. Biol. C, vol. 281, No. 8, Jan. 1, 2006, pp. 5258-5266.
Tulsi N S et al: "A protected I-bromophosphonomethylphenylalanine amino acid derivative (BrPmp) for synthesis of irreversible protein tyrosine phosphatase inhibitors", Bioorganic & Medicinal Chemistry, Pergamon, GB, vol. 18, No. 24, Dec. 15, 2010, pp. 8679-8686.
Viktor V Vintonyak et al: "Using small molecules to target protein phosphatases", Bioorganic & Medicinal Chemistry, Pergamon, GB, vol. 19, No. 7, Feb. 23, 2011, pp. 2145-2155.
Navasona Krishnan et al: "PTP1B inhibition suggests a therapeutic strategy for Rett syndrome", Journal of Clinical Investigation, vol. 125, No. 8, Jul. 27, 2015, pp. 3163-3177.
Nicholas K. Tonks, "Protein Tyrosine Phosphatases: From Housekeeping Enzymes to Master-Regulators of Signal Transduction", National Institutes of Health, Author Manuscript, Published in final edited form as: FEBS J. Jan. 2013; 280(2): 346-378.
Sunita Venkateswaran et al: "Adolescent onset cognitive regression and neuropsychiatric symptoms associated with the A140V MECP2 mutation", Developmental Medicine & Child Neurology, 2014, 56: 91-94.
Theodore O. Johnson, et al. "Protein Tyrosine Phosphatase 1B Inhibitors for Diabetes", Reviews, Nature Publishing Group, Sep. 2002, vol. 1, pp. 696-709.
Aftabul Haque, et al., "Conformation-Sensing Antibodies Stabilize the Oxidized Form of PTP1B and Inhibit Its Phosphatase Activity", National Institutes of Health, Author Manuscript, Published in final edited form as: Cell. Sep. 30, 2011; 147(1): 185-198.
Jacky Guy, et al., "A mouse Mecp2-null mutation causes neurological symptoms that mimic Rett syndrome", letter, nature genetics, vol. 27, Mar. 2001, pp. 322-326.
Ruthie E. Amir, et al., "Rett syndrome is caused by mutations in X-linked MECP2, encoding methyl-CpG-binding protein 2", letter, nature genetics, vol. 23, Oct. 1999, pp. 185-188.
Thierry Bienvenu, et al., "Rett syndrome is caused by mutations in X-linked MECP2, encoding methyl-CpG-binding protein 2", Human Molecular Genetics, 2000, vol. 9, No. 9, pp. 1377-1384.
Mimi Wan, et al., "Rett Syndrome and Beyond: Recurrent Spontaneous and Familial MECP2 Mutations at CpG Hotspots", Am. J Hum Genet. 65:1520-1529, 1999.
Omar S. Khwaja, et al., "Safety, pharmacokinetics, and preliminary assessment of efficacy of mecasermin (recombinant human IGF-1) for the treatment of Rett syndrome", PNAS 2014.
Kathleen A. Kenner, et al., "Protein-tyrosine Phosphatase 1B Is a Negative Regulator of Insulin- and Insulin-like Growth Factor-I-stimulated Signaling", The Journal of Biological Chemistry, vol. 271, No. 33, Issue of Aug. 16, pp. 19810-19816, 1996.
Gaofeng Fan, et al., "Protein-tyrosine Phosphatase 1B Antagonized Signaling by Insulin-like Growth Factor-1 Receptor and Kinase BRK/PTK6 in Ovarian Cancer Cells", The Journal of Biological Chemistry vol. 288, No. 34, pp. 24923-24934, Aug. 23, 2013.
Deirdre A. Buckley, et al., "Regulation of Insulin-Like Growth Factor Type I (IGF-I) Receptor Kinase Activity by Protein Tyrosine Phosphatase 1B (PTP-1B) and Enhanced IGF-I-Mediated Suppression of Apoptosis and Motility in PTP-1B-Deficient Fibroblasts", Molecular and Cellular Biology, Apr. 2002, vol. 22, No. 7pp. 1998-2010.

(Continued)

*Primary Examiner* — Pancham Bakshi
(74) *Attorney, Agent, or Firm* — Fox Rothschild LLP

(57) ABSTRACT

The present invention relates to agents and methods for treating autism spectrum disorders, such as Rett Syndrome.

8 Claims, 14 Drawing Sheets

(56) References Cited

OTHER PUBLICATIONS

Christophe Blanquart, et al., "Monitoring the Activation State of the Insulin-Like Growth Factor-1 Receptor and Its Interaction with Protein Tyrosine Phosphatase 1B Using Bioluminescence Resonance Energy Transfer", Molecular Pharmacology, 2005, vol. 68, No. 3, pp. 885-894.

Ozek et al., "Protein-tyrosine Phosphatase 1B (PTP1B) Is a Novel Regulator of Central Brain-derived Neurotrophic Factor and Tropomyosin Receptor Kinase B (TrkB) Signaling", The Journal of Biological Chemistry vol. 289, No. 46, pp. 31682-31692, Nov. 14, 2014.

Ozek et al., "novel role for PTP1B in BDNF/TrkB signaling in the context of metabolism", Neuroscience 2013, Nov. 11, 2013, Presentation abstract.

Li and Pozzo-Miller, "BDNF deregulation in Rett syndrome", Published in final edited form as: Neuropharmacology, 2014, 76(00).

* cited by examiner

TREATMENT OF RETT SYNDROME

CROSS-REFERENCE TO RELATED APPLICATIONS

This application is a Divisional of U.S. patent application Ser. No. 15/514,415, filed on Mar. 24, 2017, which is the U.S. national phase application of International Patent Application No. PCT/US2015/051594, filed on Sep. 23, 2015, which claims the benefit of priority of U.S. Provisional Application No. 62/055,433, filed on Sep. 25, 2014 and U.S. Provisional Application No. 62/185,214, filed on Jun. 26, 2015, the disclosures of which are incorporated hereby by reference in their entireties.

STATEMENT REGARDING FEDERALLY SPONSORED RESEARCH

This invention was made with government support under Grant Number GM055989 awarded by The National Institutes of Health. The government has certain rights in the invention.

FIELD OF THE INVENTION

This invention relates to agents and methods for treating or ameliorating symptoms of autism spectrum disorders, such as Rett Syndrome.

BACKGROUND OF THE INVENTION

Autism spectrum or autistic spectrum disorders are a range of neurological disorders that are characterized by social deficits and communication difficulties, stereotyped or repetitive behaviors and interests, and in some cases, cognitive delays. Examples of the disorders include autism, Asperger syndrome, pervasive developmental disorder not otherwise specified (PDD-NOS), childhood disintegrative disorder, and Rett syndrome. See Diagnostic and Statistical Manual of Mental Disorders 5th edition, American Psychiatric Association, May 18, 2013 and Lord et al, Autism Spectrum Disorders. *Neuron.* 2000; 28(2):355-63.

Rett Syndrome is characterized by normal early growth and development followed by a slowing of development, loss of purposeful use of the hands, distinctive hand movements, slowed brain and head growth, problems with walking, seizures, and intellectual disability. Nearly all cases of Rett Syndrome are caused by a mutation in the methyl CpG binding protein 2, or MECP2 gene. The MECP2 gene is found on a person's X chromosome, one of the two sex chromosomes. Since males have only one X chromosome, those with defects in their MECP2 genes frequently do not show clinical features of Rett syndrome but experience severe problems when they are first born and die shortly after birth. Females have two X chromosomes, but only one is active in any given cell. As a result, Rett Syndrome patents are almost exclusively females and it is estimated that Rett Syndrome affects one in every 10,000 to 15,000 live female births and in all racial and ethnic groups worldwide. See, e.g., Rett Syndrome Fact Sheet by National Institute of Neurological Disorders and Stroke available at /www.n-inds.nih.gov/disorders/rett/detail_rett.htm.

Currently there is no cure for Rett Syndrome. Treatment for the disorder is symptomatic, i.e., focusing on the management of symptoms, and supportive, requiring a multidisciplinary approach. For example, medication may be used for breathing irregularities and motor difficulties, and anticonvulsant drugs may be used to control seizures. Also, occupational therapy is used to help children develop skills needed for performing self-directed activities (such as dressing, feeding, and practicing arts and crafts), while physical therapy and hydrotherapy may prolong mobility. See, e.g., Rett Syndrome Fact Sheet, supra. There is a need for agents and methods for treating Rett Syndrome as well as other autism spectrum disorders.

SUMMARY OF INVENTION

This invention addresses the need mentioned above by providing agents and methods for treating or ameliorating symptoms of neurologic diseases, such as autism spectrum disorders and Rett Syndrome.

In one aspect, the invention provides a method for treating a neurologic disease associated with one or more mutations in the MECP2 gene. More broadly, the invention provides a method for treating neurologic diseases, including autism spectrum disorders, associated with increased intercellular expression of PTP1B or intracellular activity of PTP1B, or both. The method includes administering to a subject (e.g., a human patient) in need thereof an effective amount of a therapeutic agent that is an inhibitor of protein-tyrosine phosphatase 1B (PTP1B). The inhibitor of PTP1B can be a small molecule compound, a nucleic acid, or a polypeptide. Examples of the small molecule compound include CPT157633, a triterpene such as ursolic acid (UA001) or UA0713, and derivatives of each of these compounds. In one embodiment, the neurologic disease is an autism spectrum disorder. In one example, the autism spectrum disorder is Rett Syndrome. In certain embodiments, in treating the neurologic disorder, the therapeutic agent is administered to the subject only after diagnosis of the neurologic disease as one associated with one or more mutations in the MECP2 gene. For example, the diagnosis can include testing the subject for a mutation in a gene encoding methyl CpG-binding protein 2 (MECP2). More specifically, the diagnosis can be that of an autism spectrum disorder. In one example, the diagnosis can be that of Rett Syndrome.

In a second aspect, the invention provides a system containing (i) a first pharmaceutical composition having an effective amount of a first therapeutic agent that is an inhibitor of PTP1B, and (ii) a kit or reagent for diagnosing an autism spectrum disorder. In one embodiment, the kit allows one to detect a mutation in a gene encoding MECP2. To that end, the kit can include PCR primers for obtaining an amplicon of the gene or a transcript therefrom encompassing the locus of the mutation. The kit can also include an oligonucleotide or probe that is capable of hybridizing to (i) a mutant or a wild type form of the gene or (ii) the complement thereof under a high stringency condition. To facilitate detection, the oligonucleotide or probe can be labeled with a reporter molecule. In a preferred embodiment, the system can further include a second pharmaceutical composition comprising an effective amount of a second therapeutic agent. This second therapeutic agent can be an IGF1 or an analog thereof.

In a third aspect, the invention features a pharmaceutical composition containing (i) an effective amount of a first therapeutic agent that is an inhibitor of PTP1B, (ii) an effective amount of a second therapeutic agent that is an IGF1 or an analog thereof, and (iii) a pharmaceutically acceptable carrier.

In another aspect, the present invention provides a composition comprising an inhibitor of PTP1B for use in treatment of a neurologic disorder characterized by mutations in the MECP2 gene.

The details of one or more embodiments of the invention are set forth in the description below. Other features, objectives, and advantages of the invention will be apparent from the description and from the claims.

DETAILED DESCRIPTION OF THE INVENTION

Figure 1:
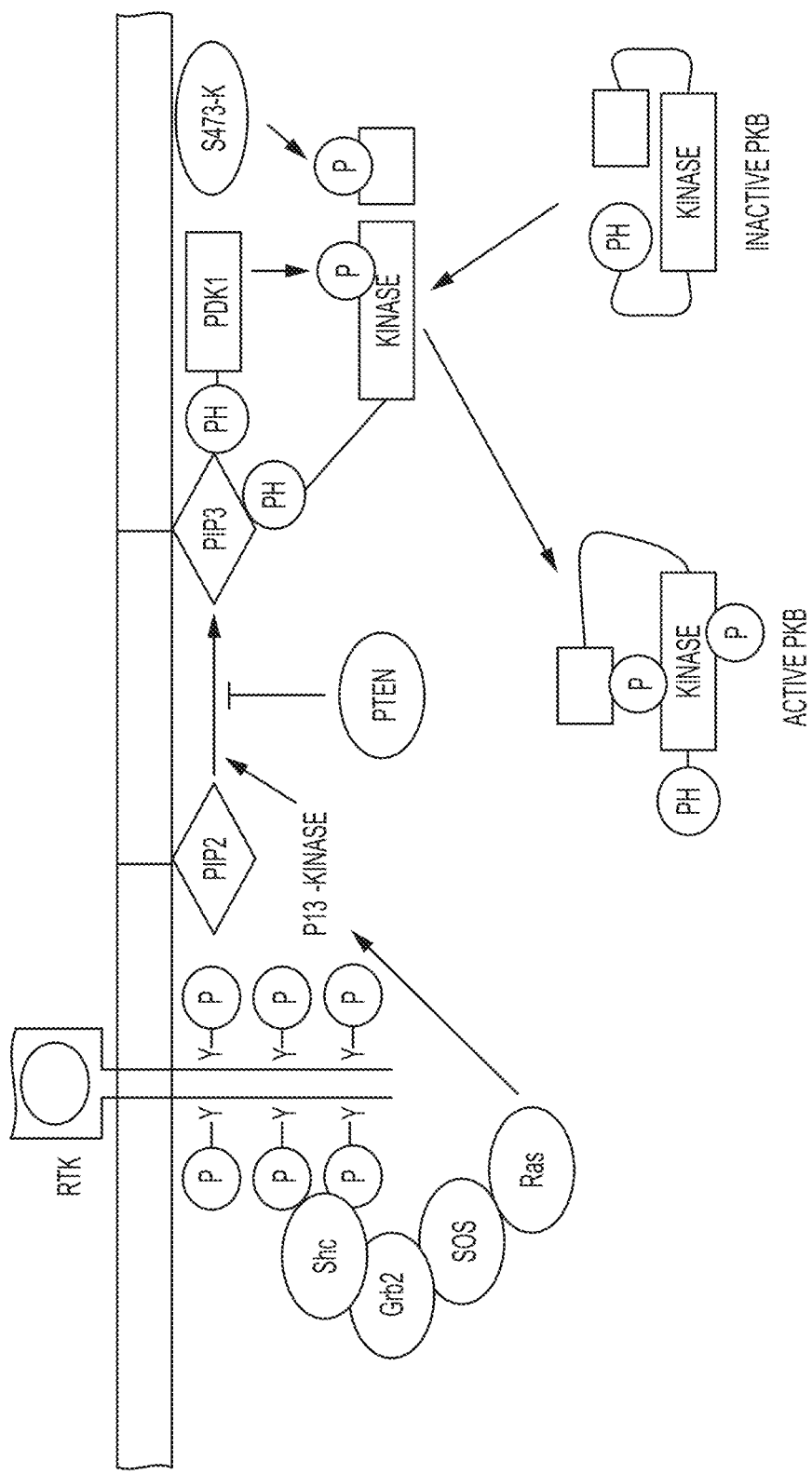
FIG. 1 is a diagram showing signal transduction pathway involving receptor tyrosine kinases (RTK)-phosphoinositide-3-kinase-protein kinase B/Akt (PI3K-PKB/Akt).

This invention is based, at least in part, on the discovery that inhibition of protein-tyrosine phosphatase 1B (PTP1B), as described herein, ameliorated a number of Rett Syndrome symptoms. Accordingly, inhibitors of PTP1B offer a new strategy for treating Rett Syndrome and other neurologic diseases, including other autism spectrum disorders, characterized by mutations in the MECP2 gene. More broadly, inhibitors of PTP1B offer a new strategy for treating neurologic diseases, including autism spectrum disorders, associated with increased intercellular expression of PTP1B or intracellular activity of PTP1B, or both.

Rett Syndrome as used herein refers to a neurologic, neurodevelopmental disorder that is characterized and caused by defects in the MECP2 gene in affected cells, e.g., one or more mutations in the gene as shown below. As noted above, nearly all cases of Rett Syndrome are caused by a mutation in the MECP2 gene, such as missense, nonsense and frameshift mutations affecting MECP2 function. Examples of the mutations include those described in Guy et al., Nat Genet. 2001 March; 27(3):322-6, Bienvenu et al., Hum Mol Genet. 2000 May 22; 9(9):1377-84, Wan et al., Am J Hum Genet. 1999 December; 65(6):1520-9, and Amir et al., Nat Genet. 1999 October; 23(2):185-8. All of these references are incorporated herein by reference in their entireties. For example, these include different MECP2 gene point mutations or deletions detected in Rett Syndrome patients constituting missense, nonsense and frameshift mutations as exemplified by Bienvenu et al. and Table 1 below.

TABLE 1

Exemplary MECP2 gene Mutations in Rett Syndrome

| Base Change | Mutations |
|---|---|
| 808C->T | R270X |
| 317G->A | R106Q |
| 502C->T | R168X |
| 473C->T | T158M |
| 880C->T | R294X |
| 916C->T | R306C |
| | 1165del26 |
| 592A->T | R198X |
| | 1194insT |
| 763C->T | R255X |
| | 1156del17 |
| 905C->G | P302R |
| 1038C->G | P322A |
| 1461A->C | X487C |
| | 677insA |
| | 1163del26 |
| | 1158del10 |
| 316C->T | R106W |
| 397C->T | R133C |
| 464T->C | F155S |
| 411delG | L138X |
| 620insT | E235X |
| 806delG | V288X |

PTP1B and Related Signal Transduction Pathway

The protein tyrosine phosphatase PTP1B is an enzyme that is the founding member of the protein tyrosine phosphatase (PTP) family. Protein tyrosine phosphatases are a group of enzymes that remove phosphate groups from phosphorylated tyrosine residues on proteins. See, e.g., US Patent Application Publication 20130029366. The amino acid sequences and related nucleic sequences of exemplary PTP1B are described, for example, under GenBank Accession NOs. NM_002827, NP_002818, BT006752, AAP35398, M31724, AAA60223, M33689, AAA60157, BC015660, AAH15660, BC018164, AAH18164, AK316563, BAG38152, or sequences relating to Unigene Cluster Hs. 417549 (UGID: 223337) *Homo sapiens* (human) PTPN1).

Protein tyrosine (pTyr) phosphorylation is a common post-translational modification that can create recognition motifs for protein interactions and cellular localization, affect protein stability, and regulate enzyme activity. These enzymes are key regulatory components in signal transduction pathways (such as the MAP kinase pathway) and cell cycle control, and are important in the control of cell growth, proliferation, differentiation and transformation. See e.g., Hemmings et al., Cold Spring Harb Perspect Biol 2012; 4:a011189.

Treatment Methods

As disclosed herein, PTP1B can be targeted for treating neurologic diseases associated with increased expression or activity of PTP1B, including autism spectrum disorders associated with MECP2 gene mutations, such as Rett Syndrome. Various PTP1B inhibitors can be used to practice the methods of this invention. Examples of the inhibitors include small molecule compounds, nucleic acids, and polypeptides. Such inhibitors can function at a level of enzyme activity, transcription, mRNA stability, translation, protein stability/degradation, protein modification, and protein-protein interaction. More specifically, as described herein, it has been found that PTP1B inhibitors can be used alone or in combination with other agents to ameliorate Rett Syndrome symptoms. Accordingly, one embodiment provides methods and compositions for treating Rett Syndrome.

Small Molecule Inhibitors

Many small molecule inhibitors of PTP1B are known in the art and can be used to practice the methods of treatment described herein. See e.g., U.S. Pat. Nos. 7,504,389 and 7,829,737, which are incorporated herein by reference in their entireties.

Small molecule inhibitors of PTP1B include the compounds of Formulas I and IIa-e disclosed in U.S. Pat. No. 7,504,389 and shown below:

Formula I

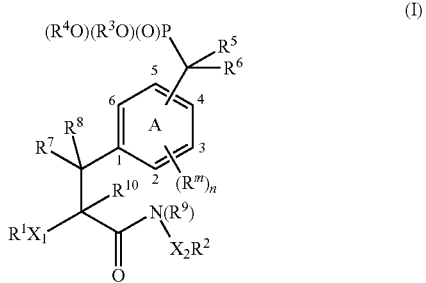

(I)

wherein:

$X_1$ is a linker group or is absent;

$X_2$ is H, absent or a linker group, preferably selected from an optionally substituted straight-chained or branched aliphatic, preferably comprising 1 to 8 carbons, optionally containing 1 or more double or triple bonds, wherein one or more of the carbons are optionally replaced by R* wherein R* is optionally substituted cycloalkyl, heterocycloalkyl, aryl or heteroaryl; —C(O)—, —C(O)C(O)—, —C(O)NR$^{11}$—, —C(O)NR$^{11}$NR$^{12}$—, —C(O)O—, —OC(O)—, —NR$^{11}$CO$_2$—, —O—, —NR$^{11}$C(O)NR$^{12}$—, —OC(O)NR$^{11}$—, —NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—, wherein R$^{11}$ and R$^{12}$ are independently selected from H and optionally substituted aliphatic, cycloalkyl, heterocycloalkyl, aryl or heteroaryl; or $X_2$ is optionally substituted cycloalkyl, heterocycloalkyl, aryl or heteroaryl; —C(O)—, —C(O)C(O)—, —C(O)NR$^{11}$—, —C(O)NR$^{11}$NR$^{12}$—, —C(O)O—, —OC(O)—, —NR$^{11}$CO$_2$—, —O—, —NR$^{11}$C(O)NR$^{12}$—, —OC(O)NR$^{11}$—, —NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—; provided that when $X_1$ is —NH—, $X_2$ is not —CH$_2$C(O)— or substituted —CH$_2$C(O)—;

R$^1$ is H or optionally substituted C$_{1-8}$ aliphatic, cycloalkyl, heterocycloalkyl, aryl or heteroaryl;

R$^2$ is H or optionally substituted C$_{1-8}$ aliphatic, cycloalkyl, heterocycloalkyl, aryl or heteroaryl; or R$_2$ is absent when $X_2$ is H;

R$^3$ and R$^4$ are independently H, alkyl or C$_{5-6}$ aryl;

R$^5$ and R$^6$ are independently H or halo;

R$^7$ and R$^8$ are independently H, —OR$^{23}$ or —NHR$^{23}$; or optionally substituted aliphatic, cycloalkyl, heterocycloalkyl, aryl or heteroaryl; or together form an optionally substituted ring comprising 3 to 7 carbon or heteroatoms;

R$^9$ is H or C$_{1-3}$ alkyl;

R$^{10}$ is H or C$_{1-3}$ alkyl; or R$^8$ and R$^{10}$ together form an optionally substituted ring comprising 3 to 7 carbon or heteroatoms; and each R$^m$ is independently H, halo, —OH, —NO$_2$, —CN; optionally substituted C$_{1-3}$ alkyl; —OR$^{23}$, —C(O)R$^{23}$, —C(O)OR$^{23}$, —C(O)N(R$^{23}$)(R$^{24}$), —OC(O)R$^{23}$, —OC(O)OR$^{23}$, —OC(O)N(R$^{23}$)(R$^{24}$), —N(R$^{23}$)(R$^{24}$), —S(O)$_2$R$^{23}$, —S(O)R$^{23}$, —SR$^{23}$, —S(O)$_2$N(R$^{23}$)(R24); NR$^{23}$C(O)R$^{24}$, —NR$^{23}$C(O)OR$^{24}$, —NR$^{23}$SOOR$^{24}$, —NR$^{23}$C(O)N(R$^{24}$)(R$^{25}$) or —NR$^{23}$SOO$_2$N(R$^{24}$)(R$^{25}$); where R$^{23}$, R$^{24}$ and R$^{25}$ are each independently H, C$_{1-4}$ alkyl or optionally substituted 3 to 8 membered cycloalkyl, heterocycloalkyl, aryl or heteroaryl; or two adjacent R$^m$ groups together form an optionally substituted aromatic or non-aromatic ring comprising 5 to 7 carbon or heteroatoms; where n is 0, 1, 2, 3 or 4; or R$^m$ and R$^7$ together form an optionally substituted aromatic or non-aromatic ring; and wherein each of the phenyl ring A carbon atoms 2-6 is optionally replaced by N; or any pair of adjacent phenyl ring A carbons atoms 2-6 is optionally replaced by S, N or O; provided that in no instance is the phenyl ring A carbon atom that is substituted with the phosphonate group replaced;

Formula IIa

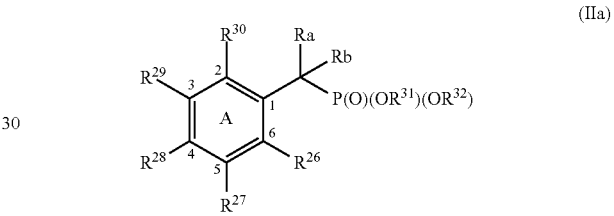

(IIa)

wherein:

R$_a$ and R$_b$ are independently H or halogen;

R$^{26}$, R$^{27}$, R$^{29}$ and R$^{30}$ are each independently H, halo, —OH, —NO$_2$, —CN, —CF$_3$, —CHF$_2$, —CH$_2$CH$_3$, —CH$_2$CF$_3$, —CF$_2$CF$_3$, —CH$_2$Cl, —CH$_2$OH, —CH$_2$CH$_2$OH, —CH$_2$NH$_2$, —CH$_2$CH$_2$NH$_2$, —CH$_2$SO$_2$CH$_3$, —OR$^{23}$, —C(O)R$^{23}$, —C(O)OR$^{23}$, —C(O)N(R$^{23}$)(R$^{24}$), —OC(O)R$^{23}$, —OC(O)OR$^{23}$, —OC(O)N(R$^{23}$)(R$^{24}$), —N(R$^{23}$)(R$^{24}$), —S(O)$_2$R$^{23}$, —S(O)R$^{23}$, —SR$^{23}$, —S(O)$_2$N(R$^{23}$)(R$^{24}$), —NR$^{23}$C(O)R$^{24}$, —NR$^{23}$C(O)OR$^{24}$, —NR$^{23}$SOOR$^{24}$, —NR$^{23}$C(O)N(R$^{24}$)(R$^{25}$), —NR$^{23}$SO$_2$R$^{24}$ or —NR$^{23}$SO$_2$N(R$^{24}$)(R$^{25}$); or optionally substituted C$_{1-6}$ alkyl, C$_{1-6}$ alkoxy or aryl; where R$^{23}$, R$^{24}$ and R$^{25}$ are each independently H, C$_{1-4}$ alkyl or C$_{3-8}$ cycloalkyl, heterocycloalkyl, aryl or heteroaryl;

R$^{31}$ and R$^{32}$ are each independently H, alkyl or C$_{5-6}$ aryl;

R$^{28}$ is H, halogen, —CN, —[CH$_2$]$_n$—[C(H)$_{3-p}$]$_x$(R$^{33}$)$_p$, —C(O)OH, —C(O)(CH$_2$)$_n$NH$_2$, —C(O)NH(CH$_2$)$_n$R$^{35}$, —C═N—N—S(O)$_2$R$^{33}$, —(CH$_2$)$_n$—CH(R$^{34}$)(R$^{35}$) or —CHNR$^{34}$; or R$^{28}$ taken together with either R$^{27}$ or R$^{29}$ form an optionally substituted ring comprising 3 to 8 carbon or heteroatoms;

each R$^{33}$ is independently H, halogen, —C(O)OR$^{39}$, —OH, —CN, —N═N—N, —N(R$^{37}$)(R$^{38}$), —C(O)NH(CH$_2$)$_n$R$^{39}$, —C(R$^{39}$)(NH$_2$)C(O)OR$^{39}$, —CH$_2$R$^{35}$ or —CH(R$^{35}$)NHS(O)$_2$R$^{39}$; or an optionally substituted cycloalkyl, heterocycloalkyl, aryl or heteroaryl;

R$^{34}$ is H or —N(R$^{37}$)(R$^{38}$);

R$^{35}$ is H, —C(O)R$^{34}$, —C(O)OR$^{39}$ or —N(NH$_2$)C(O)NH(CH$_2$)$_n$Ph;

R$^{37}$ and R$^{38}$ are each independently H, —C(O)OR$^{39}$, —C(O)cycloalkyl-Ph, —S(O)$_2$R$^{39}$, —C(O)R$^{39}$, —OC(O)R$^{39}$, —C(O)(CH$_2$)$_q$R$^{39}$, —S(O)$_2$, —S(O)$_2$NHR$^{39}$, —S(O)$_2$N(R$^{44}$)(R$^{39}$), —N(R$^{39}$)(R$^{44}$), —C(O)N(R$^{44}$)(R$^{39}$) or —NHC(O)N(R$^{44}$)(R$^{39}$); or optionally substituted C$_{1-6}$ alkyl, $C_{3-8}$ cycloalkyl, $C_{5-8}$ aryl, 3 to 8 membered heterocycloalkyl or 5 to 8 membered heteroaryl; and $R^{39}$ and $R^{44}$ are each independently H or optionally substituted $C_{1-6}$ alkyl, $C_{3-8}$ cycloalkyl, $C_{5-8}$ aryl, 3 to 8 membered heterocycloalkyl or 5 to 8 membered heteroaryl;

wherein each of the phenyl ring A carbon atoms 2-6 including its respective substituents is optionally replaced by N; or any pair of adjacent phenyl ring A carbons atoms 2-6 and their respective substituents are optionally replaced by S, N or O; and wherein n is an integer from 0 to 4; m is 0, 1 or 2; p is an integer from 1 to 3; q is an integer from 0 to 6; and x is either 0 or 1, provided that when x is 0, p is 1;

Formula IIb

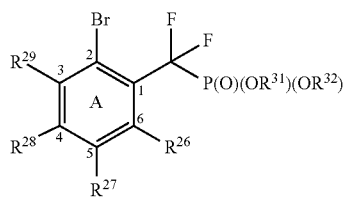

(IIb)

wherein $R^{26}$, $R^{27}$, $R^{28}$, $R^{29}$, $R^{31}$ and $R^{32}$ are as defined above; each of the phenyl ring A carbon atoms 3-6 including its respective substituents is optionally replaced by N; or any pair of adjacent phenyl ring A carbons atoms 3-6 and their respective substituents are optionally replaced by S, N or O;

Formula IIc

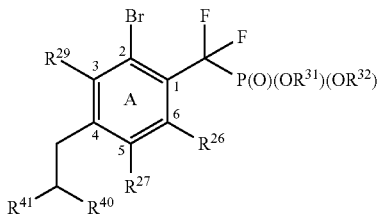

(IIc)

wherein $R^{26}$, $R^{27}$, $R^{29}$, $R^{31}$ and $R^{32}$ are as defined above for Formula IIa;

$R^{40}$ is H, alkyl, alkylene, —C(O)OR$^{39}$, —C(O)N(R$^{37}$)(R$^{38}$) or —N(NH$_2$)C(O)NH(CH$_2$)$_n$Ph;

$R^{41}$ is —N(R$^{37}$)(R$^{38}$); wherein $R^{37}$ and $R^{38}$ are as described above for Formula IIa; and each of the phenyl ring A carbon atoms 3, 5 or 6 including its respective substituents is optionally replaced by N; or phenyl ring A carbons atoms 5 and 6 together and their respective substituents is optionally replaced by an S, N or O;

Formula IId

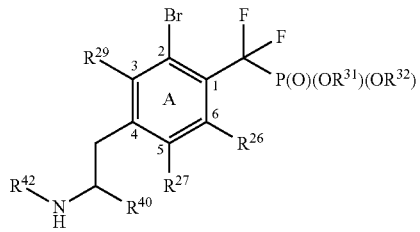

(IId)

wherein $R^{26}$, $R^{27}$ and $R^{29}$ are as defined above for Formula IIa;

$R^{31}$ and $R^{32}$ are each independently H, alkyl or $C_{5-6}$ aryl; $R^{40}$ is as defined above for Formula IIc; $R^{42}$ is H, optionally substituted $C_{1-3}$ alkyl, —C(O)OR$^{39}$, —OC(O)R$^{39}$, —C(O)N(R$^{44}$)(R$^{39}$), —C(O)cyclopropyl-Ph, —S(O)$_2$R$^{39}$, —S(O)$_2$NHR$^{39}$ or —C(O)(CH$_2$)$_q$R$^{39}$; and each of the phenyl ring A carbon atoms 3, 5 or 6 including its respective substituents are optionally replaced by N; or phenyl ring A carbons atoms 5 and 6 together and their respective substituents are optionally replaced by an S, N or O; and wherein $R^{39}$ is as defined above for Formula IIa; and Formula IIe

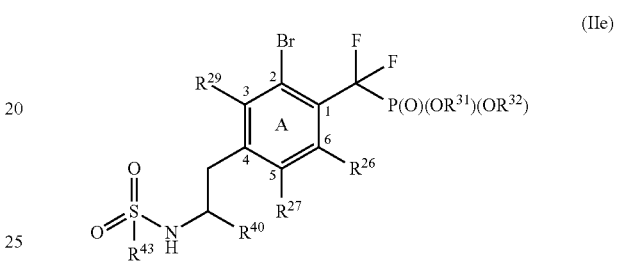

(IIe)

wherein $R^{26}$, $R^{27}$, $R^{29}$ and $R^{40}$ are as defined above for Formula IId; and $R^{31}$ and $R^{32}$ are each independently H, alkyl or $C_{5-6}$ aryl; $R^{43}$ is H, —NHR$^{39}$ or is $R^{39}$; wherein $R^{39}$ is H or optionally substituted $C_{1-6}$ alkyl, $C_{3-8}$ cycloalkyl, 3-8 member heterocycloalkyl, $C_{3-8}$ aryl or 3 to 8 membered heteroaryl; and each of the phenyl ring A carbon atoms 3, 5 or 6 including its respective substituents is optionally replaced by N; or phenyl ring A carbons atoms 5 and 6 together and their respective substituents are optionally replaced by S, N or O.

In some examples, the inhibitor can be one selected from the group consisting of {[2-bromo-4-(2-carbamoyl-2-methanesulfonylaminoethyl)phenyl]difluoromethyl}-phosphonic acid (CPT157633, Ceptyr, Inc), or a derivative and analog of CPT157633. In some examples, the inhibitor can be one selected from ursolic acid (UA001) or UA0713, or another triterpene derivative or analog. See Zhang et al, Biochimica Biophys. Acta, (2006), 1760:1505-1512. The term "derivative" refers to a chemical compound that is similar to another compound in structure and function. The derivative may differ structurally by a single element or group, or by modification of more than one group (e.g., 2, 3, or 4 groups) if it retains the same function as the parent compound. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Also, moieties may be added to the agents described herein to alter their pharmacokinetic properties, such as to increase half-life in vivo or ex vivo, or to increase cell penetration properties or bioavailability. Also included are prodrugs, which are known to enhance numerous desirable qualities of pharmaceuticals (e.g., solubility, bioavailability, manufacturing, etc.). The term "analog" refers to a compound that is a structural derivative of a parent compound that differs in respect to elemental composition such as by replacement of one atom with another, or one functional group with another.

The structure of CPT157633 is shown below:

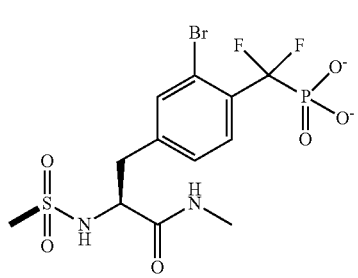

Derivatives and analogs of CPT157633 include compounds having the formulas of Formulas I and II(a)-(e).

The structure of Ursolic acid (UA001) is shown below:

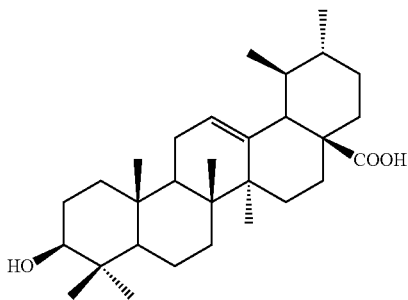

Ursolic Acid

The structure of UA0713 is shown below:

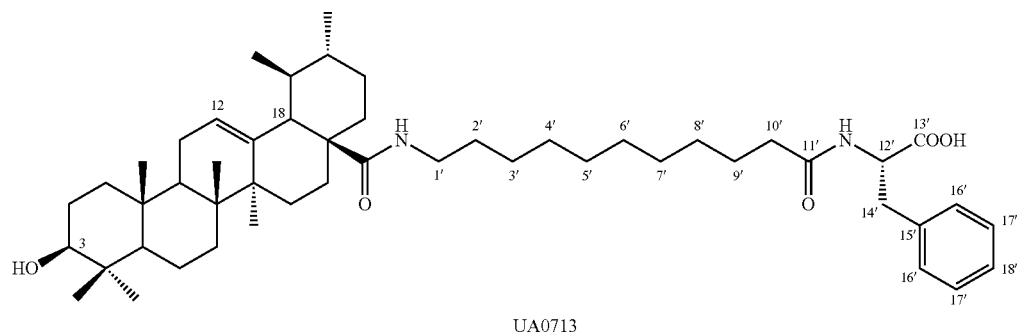

UA0713

Triterpene inhibitors of PTP1B include those shown in Table 2 below.

TABLE 2

| Triterpene inhibitors of PTP1B | | | |
|---|---|---|---|
| Triterpene name and structure | Ki (µM), PTP1B$_{405}$ | Ki (µM), PTP1B$_{321}$ | Reversibility |
| 18β-Glycyrrhetinic acid | 10 | 10 | Reversible |

TABLE 2-continued
Triterpene inhibitors of PTP1B
| Triterpene name and structure | Ki (μM), PTP1B$_{405}$ | Ki (μM), PTP1B$_{321}$ | Reversibility |
| --- | --- | --- | --- |
| 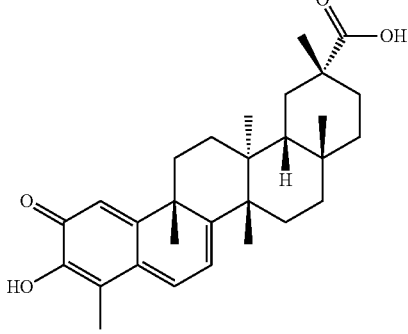  Celastrol | 10 | 10 | Irreversible |
| 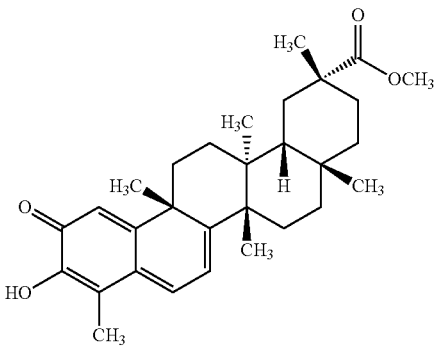  Pristimerin | 8 | 10 | Irreversible |
| 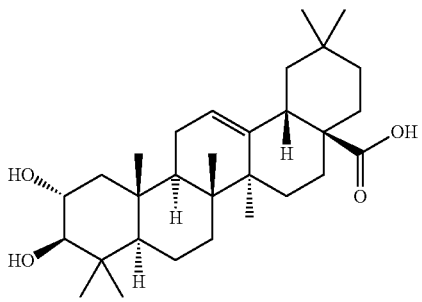  Maslinic acid | 5.7 | 10 | Reversible |
| 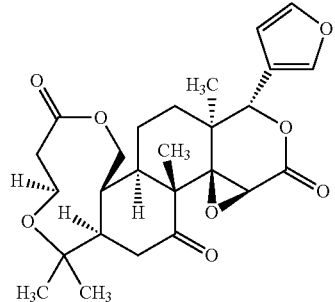  Limoni | 6 | 9 | Reversible |

TABLE 2-continued
Triterpene inhibitors of PTP1B
| Triterpene name and structure | Ki (μM), PTP1B$_{405}$ | Ki (μM), PTP1B$_{321}$ | Reversibility |
|---|---|---|---|
| 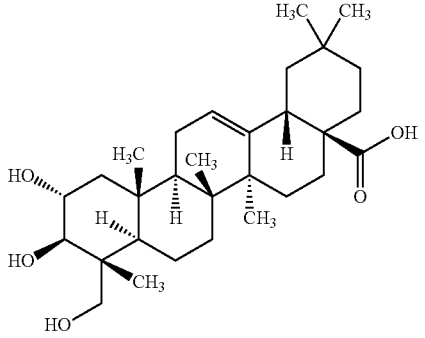<br>Arjunolic acid | 7 | 8.3 | Reversible |
| 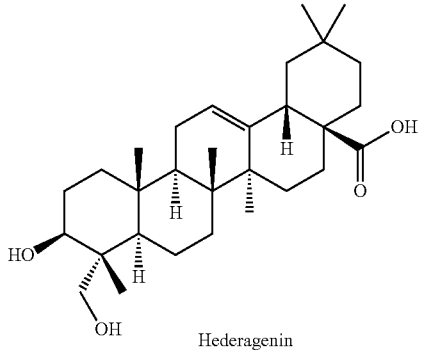<br>Hederagenin | 2 | 3.6 | Reversible |
| 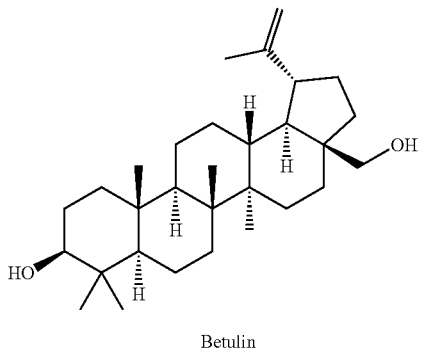<br>Betulin | 2 | 3 | Reversible |
| 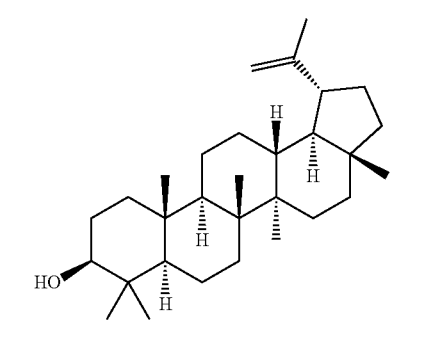<br>Lupeol | 1.5 | 2.5 | Reversible |

TABLE 2-continued
| Triterpene inhibitors of PTP1B | | | |
|---|---|---|---|
| Triterpene name and structure | Ki (µM), PTP1B$_{405}$ | Ki (µM), PTP1B$_{321}$ | Reversibility |
| 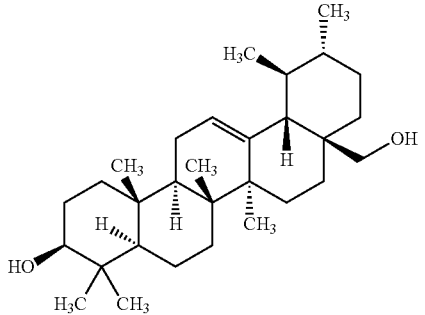 Uveol | 1 | 2.5 | Reversible |
| 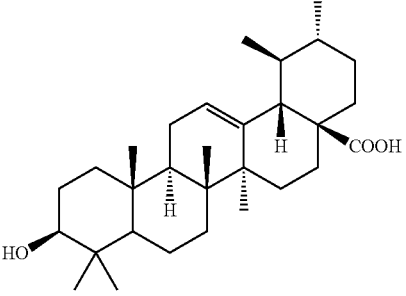 Ursolic acid | 0.9 | 2 | Reversible |
| 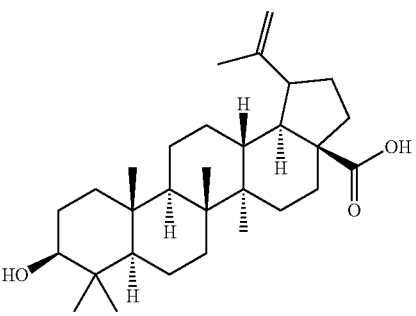 Betulinic acid | 0.7 | 3 | Irreversible |
| 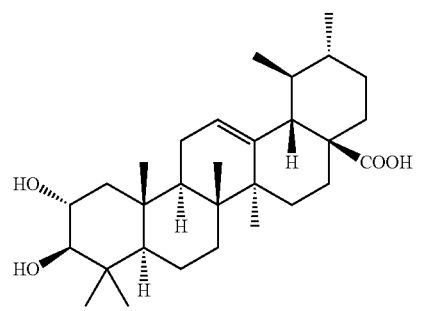 Corosolic acid | 1.5 | 3 | Irreversible |

TABLE 2-continued

Triterpene inhibitors of PTP1B

| Triterpene name and structure | Ki (μM), PTP1B$_{405}$ | Ki (μM), PTP1B$_{321}$ | Reversibility |
|---|---|---|---|
| Oleanolic acid | 2 | 4 | Reversible |
| Boswellic acid | 4 | 6 | Reversible |
| Friedelin | 2 | 4 | Reversible |
| Momordicin | 15 | 15 | Reversible |

TABLE 2-continued
Triterpene inhibitors of PTP1B
| Triterpene name and structure | Ki (μM), PTP1B$_{405}$ | Ki (μM), PTP1B$_{321}$ | Reversibility |
|---|---|---|---|
| 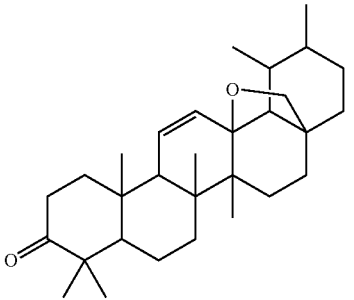 Momordicinin | 11 | 13 | Reversible |
| 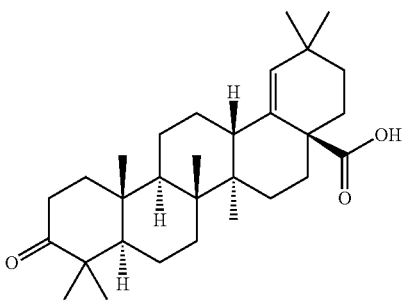 Moronic acid | 5 | 7 | Reversible |
| 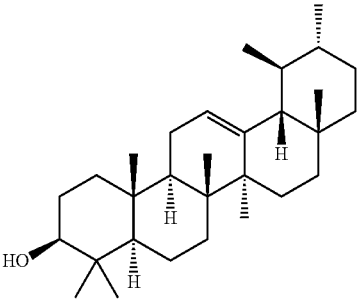 amyrin | 4 | 6 | Irreversible |
| 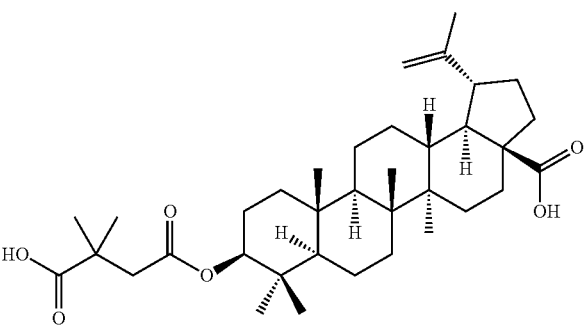 bevirimat | 4.4 | 7 | Irreversible |

TABLE 2-continued
| Triterpene inhibitors of PTP1B | | | |
|---|---|---|---|
| Triterpene name and structure | $K_i$ (μM), PTP1B$_{405}$ | $K_i$ (μM), PTP1B$_{321}$ | Reversibility |
| 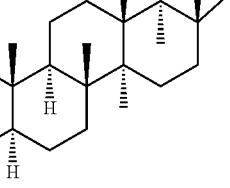 hopane | 5.7 | 9 | Reversible |
| 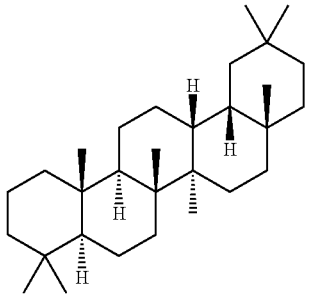 Oleanane | 9 | 15 | Reversible |
| 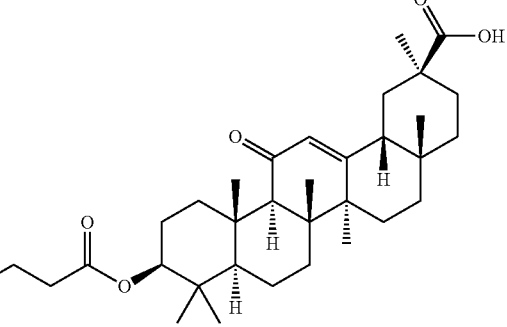 Carbenoxolone | 5 | 7 | Reversible |
| 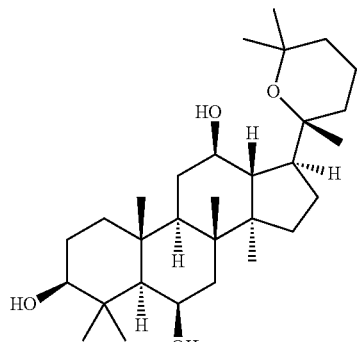 Panaxatriol | 10 | 14 | Reversible |

TABLE 2-continued

Triterpene inhibitors of PTP1B

| Triterpene name and structure | Ki (µM), PTP1B$_{405}$ | Ki (µM), PTP1B$_{321}$ | Reversibility |
|---|---|---|---|
| 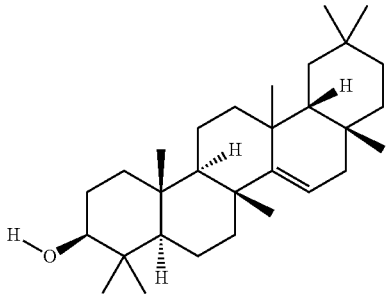 Taraxerol | 5 | 8 | Reversible |
| 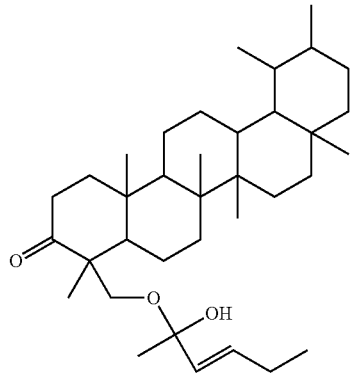 Momordicilin | 22 | 18 | Reversible |
| 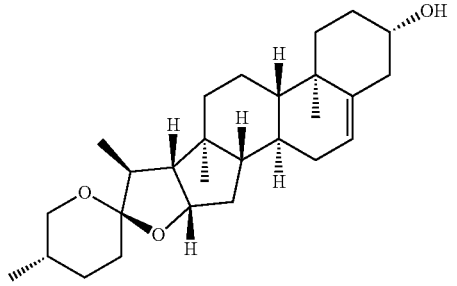 Yamogenin | 25 | 36 | Reversible |

Nucleic Acid Inhibitors

To practice the methods of treatment described herein, one can also use a nucleic acid-based inhibitor that decreases the expression or activity level of endogenous PTP1B in a subject. Examples of such inhibitors include those utilizing RNAi (RNA interference) to specifically degrade target mRNA molecules within a cell, for example, double stranded short-interfering RNAs (siRNAs), short hairpin RNA (shRNA) or single-stranded micro-RNA (miRNA), and also inhibitors such as antisense DNA or RNA molecules, such as antisense oligonucleotides (ASO). See, e.g., U.S. Pat. Nos. 7,560,438, 8,202,980, 8,420,391, and 8,445,237.

In one embodiment, a nucleic acid inhibitor can encode a small interference RNA (e.g., an RNAi agent) that targets PTP1B and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression. See, e.g., U.S. Pat. Nos. 7,560,438, 8,202,980, 8,420,391, and 8,445,237, Pillai et al., Trends in Cell Biology 17 (3):118-126, See, e.g., Paddison, et al., Genes & Development 16:948-958.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules. See, e.g., U.S. Pat. Nos. 7,560,438, 8,202,980, 8,420,391, and 8,445,237.

An antisense polynucleotide (preferably DNA) of the present invention can be any antisense oligonucleotide so long as it possesses a base sequence complementary or substantially complementary to that of the gene or RNA encoding PTP1B. The base sequence can have at least 80%, 90%, or 95% sequence identity to the complement of the gene encoding the polypeptide. These antisense DNAs can be synthesized using a DNA synthesizer. See, e.g., U.S. Pat. Nos. 8,685,368, 8,153,777, and 8,034,376.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. See, e.g., U.S. Pat. Nos. 8,685,368, 8,153,777, and 8,034,376.

The above-discussed nucleic acids encoding one or more of the RNAi agents mentioned above or can be cloned in a vector for delivering to cells in vitro or in vivo. For in vivo uses, the delivery can target a specific tissue or organ (e.g., brain). See, e.g., U.S. Pat. Nos. 8,685,368, 8,153,777, and 8,034,376.

Delivery of the nucleic acid sequences can be also achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy include, adenovirus, adeno-associated virus (AAV), herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. See, e.g., U.S. Pat. Nos. 7,732,129, 7,572,906, 6,498,033, and 6,165,990.

Compositions

Within the scope of this invention is a composition that contains a suitable carrier and one or more of the therapeutic agents described above. The composition can be a pharmaceutical composition that contains a pharmaceutically acceptable carrier.

The term "pharmaceutical composition" refers to the combination of an active agent with a carrier, inert or active, making the composition especially suitable for diagnostic or therapeutic use in vivo or ex vivo. Examples of pharmaceutically acceptable carrier include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, 18th Edition, E. W. Martin (Mack Publishing Co., Easton, Pa., 1990). A pharmaceutically acceptable carrier, after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

The above-described composition, in any of the forms described above, can be used for treating Rett Syndrome or any other autism spectrum disorder or condition, which is characterized and caused by defects in the MECP2 gene in affected cells, e.g., one or more mutations in the gene as described herein. More broadly, it can be used for treating neurologic diseases, including autism spectrum disorders, associated with increased intercellular expression of PTP1B or intracellular activity of PTP1B, or both. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. A composition for oral administration can be any orally acceptable dosage form including capsules, tablets, emulsions and aqueous suspensions, dispersions, and solutions.

A "subject" refers to a human and a non-human animal. Examples of a non-human animal include mammals, such as non-human primates (particularly higher primates), dog, rodent (e.g., mouse or rat), guinea pig, and cat. In a preferred embodiment, the subject is a human. In another embodiment, the subject is an experimental animal or animal suitable as a disease model (such as a mouse model of Rett Syndrome). A subject to be treated can be identified by standard diagnosing techniques for the disorder.

The terms "treating" or "treatment" are used interchangeably and refer to both therapeutic treatment and prophylactic or preventative measures; wherein the object is to prevent or slow down (lessen) the targeted pathologic condition or disorder. In particular, it refers to administration of a compound or agent to a subject, who has a disorder (such as Rett Syndrome), with the purpose to cure, alleviate, relieve, remedy, delay the onset of, prevent, or ameliorate the disorder, the symptom of the disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route. The exact amount required will vary from subject to subject, depending on the species, age, and general condition of the subject, the particular therapeutic agent and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

A therapeutic agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. In other embodiments, a first agent/therapy is administered prior to a second agent/therapy. Those of skill in the art understand that the formulations and/or routes of administration of the various agents/therapies used may vary.

In one embodiment, a first small molecule inhibitor of PTP1B is co-administered with a second small molecule inhibitor of PTP1B that has a different mechanism of action than the first small molecule inhibitor. For example, CPT157333 and its derivatives and analogs are competitive inhibitors of PTP1B, and UA0713 and other triterpene inhibitors are non-competitive inhibitors of PTP1B. Thus in one embodiment, a small molecule competitive inhibitor of PTP1B is co-administered with a small molecule non-competitive inhibitor of PTP1B.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, or intranasally. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

The present invention also provides a composition comprising an inhibitor of PTP1B for use in treatment of a neurologic disorder characterized by mutations in the MECP2 gene. In one embodiment, the disorder is an autism spectrum disorder associated with MECP2 gene mutations, such as Rett Syndrome. An inhibitor of PTP1B includes the inhibitors described hereinabove, such as CPT157633 and derivatives or analogs thereof.

Companion Diagnostic Assays

The method of the invention can further include a diagnostic assay to test whether a subject has a mutation in a MECP2 gene. Such an assay provides diagnostically and therapeutically important information about levels of the gene or protein expression in a diseased tissue or other patient sample and is also known as a companion diagnostic assay. See, e.g., US 20130034847, US 20090176312, and the related FDA Guidance (available at www.fda.gov/medicaldevices/deviceregulationandguidance/guidancedocuments/ucm262292.htm#).

The protein MECP2 is an abundantly expressed DNA-binding protein, located in the nucleus and associated with 5-methylcytosine (5-mC)-rich heterochromatin. Its 486 amino acids (aa) contain two known functional domains: an 84 aa methyl-CpG-binding domain (MBD) and a 104 aa transcriptional repression domain (TRD). The MBD binds to symmetrically methylated CpG dinucleotides; the TRD interacts with the corepressor Sin3A, and together they recruit histone deacetylases. The resultant deacetylation of core histones H3 and H4 compresses the chromatin, rendering it inaccessible to the transcriptional machinery. DNA-methylation dependent repression is important for X chromosome inactivation and genomic imprinting. MECP2 is expressed in all tissues and is believed to act as a global transcriptional repressor. MECP2 is essential for the normal function of nerve cells and particularly important for mature nerve cells, where it is present in high levels. The MECP2 gene is located on the long (q) arm of the X chromosome in band 28 ("Xq28"), from base pair 152,808,110 to base pair 152,878,611. See, e.g., U.S. Pat. Nos. 7,994,127 and 6,709,817.

Currently, nearly all cases of Rett Syndrome are caused by a mutation in the MECP2 gene. See, e.g., Amir et al., 1999, *Nat. Genet.* 23 (2): 185-8; Carney et al., 2003, Schanen et al., 2004, *Pediatr Neurol* 28 (3): 205-11; *Am J Med Genet* A 126 (2): 129-40; Van den Veyver et al., 2001, *Brain Dev* 23 (Suppl 1): S147-51; and Miltenberger-Miltenyi G, Laccone F, 2004, *Hum. Mutat.* 22 (2): 107-15. As the MECP2 gene does not function properly in individuals with Rett Syndrome, insufficient amounts or structurally abnormal forms of the protein are produced and can cause other genes to be abnormally expressed. The companion diagnostic assay described herein therefore can be designed to diagnose the stage or degree of Rett Syndrome and determine a therapeutic agent to which a patient is most likely to respond. More specifically, results from such an assay can be used to correlate accurate and precise expression levels of the MECP2 gene or protein within specific tissue samples of the patient or subject from whom the tissue sample was collected and preserved. This not only provides diagnostic information about the disorder, but also permits a physician or other medical professional to determine appropriate therapy for the patient.

Various mutations in the MECP2 gene have been identified. Accordingly, one skilled in the art can test whether a subject has one or more of these mutations using standard clinical diagnostic methods well known in the art. Typically these methods include obtaining a sample from the subject, which may be without limitation a tissue sample, biopsy, fluid sample (e.g., blood, urine, saliva, and cerebrospinal fluid), etc., and then subjecting the sample to the diagnostic procedure. Many well-known methodologies are available to the practitioner to analyze the sample, such as various nucleic acid detection and amplification methods, including polymerase chain reaction-based methods, and various protein detection methods, including antibody-based detection methods. In other instances it may be possible to use imaging techniques for non-invasive diagnosis. In addition to MECP2 mutations, mutations in several other genes (e.g., the CDKL5 and FOXG1 genes) also contribute to Rett Syndrome. See, e.g., Rett Syndrome Fact Sheet by National Institute of Neurological Disorders and Stroke available at/www.ninds.nih.gov/disorders/rett/detail_rett.htm.

Accordingly, the companion diagnostic assay of this invention can optionally include testing one or more of these genes.

In one aspect, the companion diagnostic assay of the invention provides qualitative and quantitative information to determine whether a subject has or is predisposed to Rett Syndrome. A subject having Rett Syndrome or prone to it can be determined based on the expression levels, patterns, or profiles of the above-described MECP2 gene or its expression products (RNAs or polypeptides) in a test sample from the subject. In other words, the products can be used as markers to indicate the presence or absence of the disorder. Diagnostic and prognostic aspects of the companion assays of the invention include methods for assessing the expression level of the products. The methods and kits allow one to detect Rett Syndrome. For example, a lack of the expression of normal wild type MECP2 gene in the sample is indicative of presence of or high risk for the disorder. Conversely, a normal expression level is indicative lack of the disorder.

The above-described methods and markers can be used to assess the risk of a subject for developing Rett Syndrome. In particular, the companion diagnostic assays of the invention can be applied to those in high risk cohort who already have certain risks so as to gain critical insight into early detection.

A change in levels of gene products associated with Rett Syndrome can be detected in cells of a subject before, or in the early stages of, the development of disease phenotypes. The treatment method of this invention therefore also includes screening a subject who is at risk of developing Rett Syndrome, comprising evaluating the level of the MECP2 gene expression or genetic mutation(s) in a suitable test sample, and optionally the levels of one or more of other markers. Accordingly, a difference or alteration of the level of the gene product, or combination of gene products, in the biological sample as compared to the level of a corresponding gene product in a control sample, is indicative of the subject being at risk for developing Rett Syndrome. The biological sample used for such screening can include a population of cells from the blood of the subject that is either normal or suspected to have the disorder. Subjects with a change in the level of one or more gene products associated with Rett Syndrome or with one or more mutations in the in the MECP2 gene are candidates for further monitoring and testing. Such further testing can comprise histological, neurological, or behavioral examination using techniques within the skill in the art.

To enhance the accuracy for the companion diagnostic assay, a subject or patent can be further evaluated based on relevant physical and neurological status. For example, one can clinically diagnose Rett Syndrome by observing signs and symptoms during a patient's early growth and development, and conducting ongoing evaluations of the patient's physical and neurological status. To that end, a pediatric neurologist, clinical geneticist, or developmental pediatrician can be consulted to confirm the clinical diagnosis of Rett Syndrome. The physician can use a highly specific set of guidelines that are divided into three types of clinical criteria: main, supportive, and exclusion, which are known in the art. See, e.g., Diagnostic and Statistical Manual of Mental Disorders 5th edition, American Psychiatric Association, May 18, 2013, and Rett Syndrome Fact Sheet by National Institute of Neurological Disorders and Stroke available at www.ninds.nih.gov/disorders/rett/detail_rett.htm.

Rett Syndrome has been categorized into four stages based on patients' ages and symptoms. Supra. While those of stages II (ages 1-4), III (ages 2-10), and IV (ages 11 and older) show particular physical and neurological status characteristic of Rett Syndrome, symptoms of patients of stag I (typically begins between 6 and 18 months of age) may be vague and are often overlooked. Supra. Accordingly, the companion diagnostic assay described above is particular desirable for these stage I young patients.

As mentioned above, Rett Syndrome and MECP2 gene mutations affect boys more severely as a boy has only one X chromosome and those with defects die shortly after birth. Accordingly, the companion diagnostic assay of this invention should be carried our much earlier in males suspected of having Rett Syndrome. For example, prenatal diagnosis or prenatal screening can be carried out in a male fetus or embryo before he is born. Common testing procedures include amniocentesis, ultrasonography including nuchal translucency ultrasound, serum marker testing, or genetic screening. Supra.

By "diagnosis" or "evaluation" refers to a diagnosis of a Rett Syndrome, a diagnosis of a stage of Rett Syndrome, a diagnosis of a type or classification of a Rett Syndrome, a diagnosis or detection of a recurrence of a Rett Syndrome, a diagnosis or detection of a regression of a Rett Syndrome, a prognosis of a Rett Syndrome, or an evaluation of the response of a treated subject to a therapy. Usually, a diagnosis of a disease or disorder is based on the evaluation of one or more factors and/or symptoms that are indicative of the disease. That is, a diagnosis can be made based on the presence, absence or amount of a factor, which is indicative of presence, or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., Rett Syndrome.

Systems and Kits

In some embodiments of this invention, the therapeutics described above can be combined with genetic or genomic testing that determine whether that individual is a carrier of a mutant gene that is known to be correlated with a autism spectrum disorder, such as Rett Syndrome. Such a personalized medicine approach can be used to discover a subject's predisposition to the disease or disorder and susceptibility to therapy, and treat the subject accordingly.

Accordingly, another aspect of the invention provides a system containing an effective amount of any of the above-described therapeutic agent (or a combination thereof) and a kit for diagnosing an autism spectrum disorder, such as Rett Syndrome. The kit may comprise a container for collecting a nucleic acid-containing sample, for example a tube for collecting blood. Kits according to the present invention may comprise containing reagents for performing diagnosis, including methods for nucleic acid amplification, copying, primer extension, detection, identification, and/or quantification. To that end, one or more of the reaction components for the methods disclosed herein can be supplied in the form of a kit for use in the detection of a target nucleic acid. In such a kit, an appropriate amount of one or more reaction components is provided in one or more containers or held on a substrate (e.g., by electrostatic interactions or covalent bonding).

The kit described herein preferably comprises reagents for PCR-based sequencing of one or more of the coding regions and exon/intron boundaries of the MECP2 gene. The kits may include one or more of the primers specific for the MECP2 gene genomic DNA or RNA described above. The kit can include one or more containers containing one or more primers. A kit can contain a single primer in a single container, multiple containers containing the same primer, a single container containing two or more different primers of the invention, or multiple containers containing different primers or containing mixtures of two or more primers. Any combination and permutation of primers and containers is encompassed by the kits of the invention.

The kit can also contain additional materials for practicing the above-described methods. The kit thus may comprise some or all of the reagents for performing a PCR reaction using the primer of the invention. Some or all of the components of the kits can be provided in containers separate from the container(s) containing the primer of the invention. Examples of additional components of the kits include, but are not limited to, one or more different polymerases, one or more primers that are specific for a control nucleic acid or for a target nucleic acid, one or more probes that are specific for a control nucleic acid or for a target nucleic acid, buffers for polymerization reactions (in 1× or concentrated forms), and one or more dyes or fluorescent molecules for detecting polymerization products. The kit may also include one or more of the following components: supports, terminating, modifying or digestion reagents, osmolytes, and an apparatus for detecting a detection probe.

The reaction components used in an amplification and/or detection process may be provided in a variety of forms. For example, the components (e.g., enzymes, nucleotide triphosphates, probes and/or primers) can be suspended in an aqueous solution or as a freeze-dried or lyophilized powder, pellet, or bead. In the latter case, the components, when reconstituted, form a complete mixture of components for use in an assay.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The systems or kits of the invention can comprise any number of additional reagents or substances that are useful for practicing a method of the invention. Such substances include, but are not limited to: reagents (including buffers) for isolating cells, reagent for lysis of cells, divalent cation chelating agents or other agents that inhibit unwanted nucleases, control DNA/RNA for use in ensuring that primers, the polymerase and other components of reactions are functioning properly, RNA isolation reagents (including buffers), amplification reaction reagents (including buffers), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in amplification or detection of target nucleic acids. In some embodiments, the kits can further include instructions to use the components in any of the methods described herein, e.g., a method using a crude matrix without nucleic acid extraction and/or purification.

The kits or system can also include packaging materials for holding the container or combination of containers. Typical packaging materials for such kits and systems include solid matrices (e.g., glass, plastic, paper, foil, microparticles and the like) that hold the reaction components or detection probes in any of a variety of configurations (e.g., in a vial, microtiter plate well, microarray, and the like).

Instructions on the use of a companion diagnostic test can be provided on written material packaged with a compound, composition, or kit of the invention. The written material can be, for example, a label. The written material can suggest conditions or genetic features relevant to Rett Syndrome or the therapeutic compounds of the invention. The instructions provide the subject and the supervising physician with the best guidance for achieving the optimal clinical outcome from the administration of the therapy. For example, a system of this invention, in addition to containing kit components, may further include instrumentation for conducting an assay, e.g. a luminometer for detecting a signal from a labeled probe and/or a magnetic device for separating nucleic acid hybridized to a capture probe.

Instructions, such as written directions or videotaped demonstrations detailing the use of the kits or system of the present invention, are optionally provided with the kit or systems. In a further aspect, the present invention provides for the use of any composition or kit herein, for the practice of any method or assay herein, and/or for the use of any apparatus or kit to practice any assay or method herein.

Optionally, the kits or systems of the invention further include software to expedite the generation, analysis and/or storage of data, and to facilitate access to databases. The kit may comprise a software package for data analysis of the physiological status of a subject to be treated, which may include reference profiles for comparison with the relevant test profile. The software includes logical instructions, instructions sets, or suitable computer programs that can be used in the collection, storage and/or analysis of the data. Comparative and relational analysis of the data is possible using the software provided.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Additional Definitions

A "nucleic acid" refers to a DNA molecule (e.g., a cDNA or genomic DNA), an RNA molecule (e.g., an mRNA or cRNA), or a DNA or RNA analog. A DNA or RNA analog can be synthesized from nucleotide analogs. The nucleic acid molecule can be single-stranded or double-stranded.

As used herein, the term "target nucleic acid" or "target sequence" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid.

As used herein the term "amplification" and its variants includes any process for producing multiple copies or complements of at least some portion of a polynucleotide, said polynucleotide typically being referred to as a "template." The template polynucleotide can be single stranded or double stranded. A template may be a purified or isolated nucleic acid, or may be non-purified or non-isolated. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotides (e.g., dNTP) capable of being incorporated into an extension product during amplification, i.e., DNA, RNA, or a derivative if DNA or RNA, which may include a label.

As used herein, the term "oligonucleotide" refers to a short polynucleotide, typically less than or equal to 300 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled with a label such as with biotin to which a streptavidin complex may later bind.

A "label" or "reporter molecule" is chemical or biochemical moiety useful for labeling a nucleic acid (including a single nucleotide), polynucleotide, oligonucleotide, or protein ligand, e.g., amino acid or antibody. Examples include fluorescent agents, chemiluminescent agents, chromogenic agents, quenching agents, radionucleotides, enzymes, substrates, cofactors, inhibitors, magnetic particles, and other moieties known in the art. Labels or reporter molecules are capable of generating a measurable signal and may be covalently or noncovalently joined to an oligonucleotide or nucleotide (e.g., a non-natural nucleotide) or ligand.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Hybridization" or "hybridize" or "anneal" refers to the ability of completely or partially complementary nucleic acid strands to come together under specified hybridization conditions (e.g., stringent hybridization conditions) in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

The term "stringent hybridization conditions" or "stringent conditions" means conditions in which a probe or oligomer hybridizes specifically to its intended target nucleic acid sequence and not to another sequence. Stringent conditions may vary depending well-known factors, e.g., GC content and sequence length, and may be predicted or determined empirically using standard methods well known to one of ordinary skill in molecular biology (e.g., Sambrook, J. et al., 1989, Molecular Cloning, A Laboratory Manual, 2nd ed., Ch. 11, pp. 11.47-11.57, (Cold Spring Harbor Laboratory Press, Cold Spring Harbor, N.Y.)).

"Stringent conditions" or "high stringency conditions" typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (sodium chloride/sodium citrate, 0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 50% formamide at 55° C., followed by a high-stringency wash consisting of 0.1×SSC containing EDTA at 55° C.

"Moderately stringent conditions" may be identified conventionally and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like, by use of manufacturer's instructions (see, e.g., Illumina system instructions).

The term "sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient or veterinary subject. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated nucleic acid, protein, membrane preparation, or cell culture.

The terms "determining," "measuring," "assessing," "testing," and "assaying" are used interchangeably and include both quantitative and qualitative measurement, and include determining if a characteristic, trait, or feature is present or not. Assessing may be relative or absolute. Assessing the presence of a target includes determining the amount of the target present, as well as determining whether it is present or absent.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

EXAMPLES

Example 1

The following materials and methods were used in the subsequent examples.

Mice.

All animal experiments were conducted using protocols approved by the Institutional Animal Care and Use Committee at CSHL. B6.129-MeCP2$^{tm1.1Bird/J}$ mice purchased from Jackson Labs (003890) were used in the study. CBA/CaJ mice were used in the pup retrieval assays.

Drug Administration.

CPT157633 (CEPTYR Inc, Bothell, Wash.) and UA0713 (TCRS LLC, Bristol, Pa.) were dissolved in sterile saline solution and administered intraperitoneally or subcutaneously. CPT157633 was given at a single dose of 5 mg/kg body weight every day and UA0713 was given at a dose of 5 mg/kg every other day. With WT and Mecp2$^{-/y}$ male mice, compound administration was initiated at P2 and with WT and Mecp2$^{-/+}$ female mice compound administration was initiated at 10-weeks of age.

Antibodies and Reagents.

All reagents were purchased from Sigma-Aldrich unless mentioned otherwise. Antibodies used in the study were against the following: PTP1B (Cat #04-1140, EP1841Y (clone), Millipore), 4G10 (Cat #05-321, 4G10 (clone), Upstate Biotechnology), pY1162/1163-IRβ (Cat #700393, 97H9L7 (clone), Invitrogen), IR-B (Cat #sc-711, C711 (clone), Santa Cruz biotechnology), flag (Cat #F3040, M1 (clone)) and Actin (Cat #A2228, AC-74 (clone) (Sigma), IRS1 (Cat #2382, 59G8 (clone)), pT308AKT (Cat #13038, D25E6 (clone)), pS473AKT (Cat #4051, 587F11 (clone)), AKT (Cat #4691, C67E7 (clone)), pTFOXO1 (Cat #2599, 4G6 (clone)), FOXO1 (Cat #2880, C29H4 (clone)), p-GSK3B (Cat #8452, D1G2 (clone)), GSK3B (Cat #12456, D5C5Z (clone)), pY705/706TRKB (Cat #4621, C50F3 (clone)), pY515TRKB (Cat #4619, C53G9 (clone)), TRKB (Cat #4603, 80E3 (clone) and MECP2 (Cat #3456, D4F3 (clone) (Cell signaling). Control and RETT patient-derived fibroblasts were obtained from Corriell repository. TRKA and TRKC expression constructs were a generous gift from Dr. Moses Chao, NYU Medical Center, NY.

Metabolic Measurements.

Glucose in tail blood was measured using a glucometer (One-Touch Basic; Lifescan, CA). For glucose tolerance tests (GTTs), mice were fasted for 10 hours and then injected with 20% D-glucose (2 mg/g body weight) and the blood glucose was monitored immediately before and at 15, 30, 60 and 120 mins following the injection. For insulin tolerance tests (ITTs), 4-h fasted animals were given insulin (0.75 mU/g) and blood glucose was measured immediately before and at 30, 60 and 120 minutes postinjection. Serum insulin, cholesterol, triglycerides (Stanbio Labs, TX), BDNF (Abnova), IGF1 and IGFBPs (R&D Systems) were determined by enzyme-linked immunosorbent assay.

ChIP and Quantitative PCR.

For ChIP, three whole mouse brains from WT male mice were used. Briefly, flash-frozen brains were ground and to the powder 1% formaldehyde was added. Fixation was continued for 15 mins at room temperature and terminated with 0.125 M glycine solution. The cells were pelleted and homogenized in a dounce homogenizer. After centrifugation, cells were resuspended in 5 ml of lysis buffer (10 mM Tris pH 8.0, 0.2% NP-40, 10 mM NaCl, Complete protease inhibitors (Roche)). The lysate was passed through a 25-gauge needle to remove lumps and incubated for an additional 15 min in 5 ml of lysis buffer. Nuclei were harvested by centrifugation (4,000×g) for 5 min and the pellet was resuspended in 2 ml of nucleus lysis buffer (50 mM Tris-HCl, 10 mM EDTA, 1% sodium dodecyl sulfate [SDS], protease inhibitors). Nuclei were lysed for 5 min at room temperature and diluted in 1 ml of ChIP dilution buffer (20 mM Tris (pH 8.0), 150 mM NaCl, 2 mM EDTA, 1% Triton, protease inhibitors). Chromatin was sonicated (5 min, duty cycle 50, output 8). Following sonication chromatin was cleared by centrifugation, precleared with protein A-Sepharose (Sata Cruz Biotechnology), and subjected to overnight immunoprecipitation with anti-MeCP2 antibody. Antibody precipitates were bound to protein A-Sepharose for 1 h and washed once (0.1% SDS, 1% Triton X-100, 2 mM EDTA, 150 mM NaCl, 20 mM Tris-HCl [pH 8]), three times with ChIP wash buffer I (0.1% SDS, 1% Triton X-100, 2 mM EDTA, 500 mM NaCl, 20 mM Tris-HCl [pH 8]), once with ChIP wash buffer III (0.25 M LiCl, 1% NP-40, 1% deoxycholate, 1 mM EDTA, 10 mM Tris-HCl [pH 8]), and three times with Tris-EDTA.

DNA-antibody precipitates were eluted twice with 1% SDS, 0.1M sodium bicarbonate, and cross links were reversed at 65° C. for 6 hours. DNA was purified with QIAGEN pcr purification kit. From the final eluate 2 μl was used for PCRs. For gene expression studies total RNA was extracted from WT and Mecp2-null male mice. RNA extracted was used to synthesize cDNA using the iScript cDNA synthesis kit (Bio-Rad, 170-8890). The cDNA synthesized from WT and Mecp2-null brain samples were used for quantitative PCR using an Applied Biosystems 7900HT instrument. RT profiler PCR arrays (Qiagen, Cat. No. 330231-006ZA and 330231-0030ZA) were used to look at changes in gene expression in insulin signaling pathway and glucose metabolism.

Identification of TrkB as a Substrate of PTP1B.

Brain lysates (1 mg/ml) obtained from saline and/or PTP1B inhibitor treated WT and Mecp2$^{-/+}$ female mice were incubated with 20 μl of His-tagged wild-type PTP1B and D181A PTP1B fusion protein coupled to beads (10 μg/μl) in the presence and absence of 1 mM pervanadate. After several washes, complexes were analyzed by immunoblotting.

Pup Retrieval Assay.

A pup retrieval assay was performed in the manner described by Lau et al. Neuroscience 2013, 43$^{rd}$ Annual Meeting of the Society for Neuroscience presentation available at http://sfn2013.conferencespot.org/55321-sn6-1.225941/t-010-1.227112/335-12-1.227119/335-12-1.227120).

PTP1B Promoter Assay.

HEK 293T cells were transfected using LipofectAMINE Reagent (Life Technologies, Inc.) according to the supplier's protocols. Typically, 1 μg of the reporter plasmid containing different lengths of the promoter was used along with 1 μg of pRL-TK (Promega), an expression vector containing cDNA encoding *Renilla* luciferase as an internal control of transfection efficiency. Approximately 1.0×10$^5$ cells were used for each transfection with LipofectAMINE Reagent (Life Technologies, Inc.) in a 24 well plate. One μg of the reporter plasmid for expression of firefly luciferase was used. Expression plasmids for either human MECP2-E1 (0.1 μg/ml), MECP2-E2 (0.1 μg/ml), or control plasmid without insert (0.1 μg/ml) were co-transfected. Cells were incubated with DNA-lipid complex for 24 h and washed with phosphate-buffered saline, and luciferase activity was assayed using the Dual-Luciferase Reporter Assay System (Promega).

Paw-Clasping Assay.

For the paw-clasping assay, mice were suspended by their tails and observed for 30 s. The duration for which animals clasped their paws was used to calculate the percentage (paw clasping (%)=(time spent clasping paws (s)/30 (s))×100). Age-matched mice (Mecp2$^{-/-}$ vehicle, n=18; CPT157633 treated n=18) were used. Error bars represent SEM. Statistical analysis was performed using paired t test, P=0.001.

Rotarod Performance.

An increasing angular-speed rotarod system (Accuscan instruments) was used on 12- to 14-week-old female mice. Both WT and Mecp2$^{-/-}$ mice were acclimated to the testing apparatus with three 90-s trials of steadily increasing speed (4-6 rpm). Following this acclimation, four trials were conducted. These trials were repeated the following day without an acclimation period. The latency to fall for each trial was recorded. Error bars represent SEM. Statistical analysis was performed using ANOVA, P=0.01.

Protein Expression and Purification for NMR Studies.

The PTPT1B catalytic domain (residues 1-301; PTP1B$_{1\text{-}301}$) was expressed in *E. coli* and purified as previously described by Krishnan et al. (2014) Nature Chemical Biology 10:558-66. Briefly, isotope-labeled PTP1B$_{1\text{-}301}$ was expressed in *E. coli* cultures grown in M9 minimal media containing 1 g/L $^{15}$N NH$_4$Cl, 100% D$_2$O and either 4 g/L of $^{13}$C-D-glucose or $^{12}$C-D-glucose. Cultures were grown at 37° C. to an OD$_{600}$ of ~0.6 under vigorous shaking (250 rpm). Protein expression was induced with the addition of 1 mM IPTG and cultures were incubated for ~20 hours at 18° C., 250 rpm. Protein yields were ~46 mg/L in Luria broth, ~34 mg/L in $^2$H, $^{15}$N M9 medium and ~17 mg/L in $^2$H,$^{15}$N, $^{13}$C M9 medium. PTP1B$_{1\text{-}301}$ was purified by Ni$^{2+}$-affinity chromatography and size exclusion chromatography (SEC, Superdex 75 26/60), with 50 mM HEPES pH 6.8, 150 mM NaCl, 0.5 mM TCEP as the final NMR buffer.

NMR Spectroscopy.

NMR data were collected on Bruker AvanceIIIHD 850 MHz spectrometer equipped with a TCI HCN Z-gradient cryoprobe at 298 K. NMR measurements of PTP1B$_{1\text{-}301}$ were recorded using either $^2$H,$^{15}$N- or $^2$H,$^{15}$N,$^{13}$C-labeled protein at a final concentration of 0.2 mM in 50 mM HEPES pH 6.8, 150 mM NaCl, 0.5 mM TCEP and 90% H$_2$O/10% D$_2$O. The sequence-specific backbone assignment of PTP1B$_{1\text{-}301}$ in the CPT157633 bound state was achieved using the following experiments at 850 MHz $^1$H Larmor frequency: 2D [$^1$H,$^{15}$N] TROSY, 3D TROSY-HNCA, and 3D TROSY-HN(CO)CA. Assignment and titration spectra were processed with Topspin 3.1 (Bruker, Billerica, Mass.) and data were evaluated using SPARKY (http://www.c-gl.ucsf.edu/home/sparky/).

NMR Analysis of Inhibitor Binding.

CPT157633 was titrated into 200 μM [$^2$H,$^{15}$N]-PTP1B at molar ratios of 0.1:1, 0.2:1, 0.4:1, 0.5:1, 1:1, 1.5:1, 3:1 and 5:1 CPT157633:PTP1B$_{1\text{-}301}$ and 2D [$^1$H,$^{15}$N] TROSY spectra were recorded for each titration point. CPT157633 was solubilized in water at 100 mM. Chemical shift differences (Dd) between PTP1B$_{1\text{-}301}$ and CPT157633 bound PTP1B$_{1\text{-}301}$ (1.5:1 molar ratio) spectra were calculated using the following equation:

$$\Delta\delta(\text{ppm}) = \sqrt{(\Delta\delta_H)^2 + \left(\frac{\Delta\delta_N}{10}\right)^2}$$

All chemical shifts for CPT157633 bound PTP1B were deposited in the BioMagResBank (http://www.bmrb.wisc.edu) under accession number 25375.

Crystallization and Structure Determination.

PTP1B$_{1\text{-}301}$ was purified as previously described (Id.) with the exception that the final protein buffer was 20 mM Tris pH 7.5, 25 mM NaCl, 0.2 mM EDTA, 0.5 mM TCEP. CPT157633 (10:1 molar ratio) was added to PTP1B to form PTP1B$_{1\text{-}301}$:CPT157633 and the protein:ligand complex concentrated to 50 mg/mL for crystallization. Crystals of PTP1B$_{1\text{-}301}$:CPT157633 were obtained using sitting drop vapor diffusion in 0.1 M Tris, pH 7.4, 20% PEG8000, 0.2 M MgCl$_2$. The small initial crystals were used as seeds for subsequent crystallization trials in the same mother liquor. Crystals were cryo-protected by a 10 second soak in mother liquor supplemented with 30% glycerol and 10% CPT157633 (100 μM) and immediately flash frozen in liquid nitrogen. X-ray data were collected on a single crystal at 112 K using a Rigaku FR-E+ Superbright rotating copper anode X-ray generator with a Saturn 944 HG CCD detector (Brown University Structural Biology Facility) and the data processed to 1.9 Å. The PTP1B$_{1\text{-}301}$:CPT157633 data were phased using molecular replacement (Phaser as implemented in PHENIX (Adams et al. (2010) *Acta crystallographica Section D, Biological crystallography*. 66(Pt 2):213-21)) using PTP1B (PDBID: 1C88, (Iverson et al. (2000) *The Journal of Biological Chemistry* 275:10300-7)) as the search model. Clear electron density for the bound CPT157633 was visible in the initial maps. The initial model of PTP1B$_{1\text{-}301}$:CPT157633 was built using Phenix.AutoBuild (Adams et al.), followed by iterative rounds of refinement in PHENIX and manual building using Coot (Emsley et al. (2004) *Acta crystallographica Section D, Biological crystallography*. 60(Pt 12): 2126-32). The Restraint file for the CPT157633 ligand was generated using Phenix.eLBOW (Adams et al.) using the CPT157633 smiles string CNC(=O)[C@H](Cc1ccc(C(F)(F)P(=O)(O)O)c(Br)c1)NS(C)(=O)=O. Data collection and refinement statistics are reported in Supplemental Table 2. All coordinates for CPT157633 bound PTP1B were deposited in the PDB under accession number 4Y14.

Statistics.

All results are expressed as mean±SEM. ANOVA and student's t-test (two-tailed) were used to determine statistical significance; P value of 0.05 and below was considered significant. All statistical analysis and generation of graphs was performed using GraphPad Prism (version 7; GraphPad Software).

Example 2

Figure 2A:
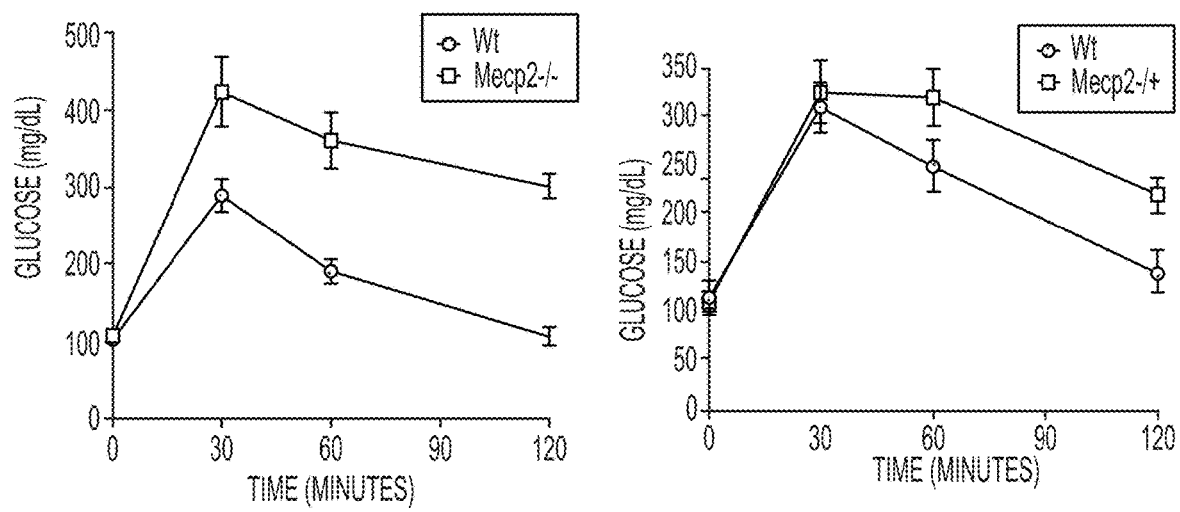
FIGS. 2A and B show that Mecp2$^{-/-}$ male and Mecp2$^{-/+}$ female mice exhibit (A) glucose intolerance and (B) symptoms of hyperinsulinemia.
Figure 2B:
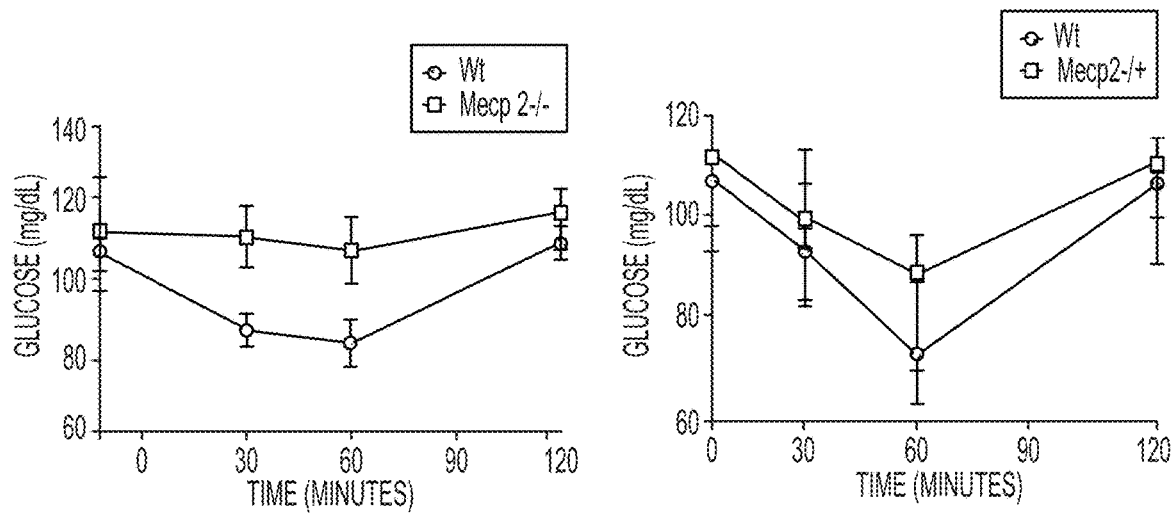

Glucose and insulin tolerance tests (GTT and ITT) were performed in both male Mecp2$^{-/y}$ and female Mecp2$^{-/+}$ mice. The hemizygous male Mecp2$^{-/y}$ mice exhibited glucose intolerance and cleared glucose at very slow rate compared to the control wild type mice. The heterozygous female Mecp2$^{-/+}$ mice were also found to be glucose intolerant (FIG. 2A). Studies were performed to determine whether the Mecp2 knockout mice respond to insulin like the WT mice. It was found that in both Mecp2$^{-/y}$ and Mecp2$^{-/+}$ blood glucose levels did not respond to the insulin administered (FIG. 2B). Glucose and insulin intolerance were observed both in Mecp2$^{-/y}$ and Mecp2$^{-/+}$ mice, however it was more pronounced in male Mecp2$^{-/y}$ mice, which can be explained by the difference in Mecp2 expression levels. It was also found that insulin levels were higher in both Mecp2$^{-/y}$ and Mecp2$^{-/+}$ mice compared to their WT counterparts. To further characterize this, the insulin signaling pathway in both Mecp2$^{-/y}$ and Mecp2$^{-/+}$ mice was studied. It was found that Mecp2 KO mice showed reduced insulin signaling characterized by reduced tyrosine phosphorylation of the insulin receptor (IR-β) and insulin receptor substrate-1 (IRS1). Recruitment of the phosphorylated IRS1 to the receptor triggers activation of phosphatidylinositol 3-Kinase (PI3K) and stimulation of downstream signaling molecules such as PKB/AKT, which results in the translocation of glucose transporter and glucose uptake and inactivation of glycogen synthase kinase (GSK30). Hence the phosphorylation of the kinase AKT and downstream signaling were studied. In contrast to the WT mice, Mecp2$^{-/y}$ mice displayed diminished phosphorylation of AKT and its substrates FOXO and GSK-3β. The Mecp2 mutant mice have higher levels of circulating levels of insulin, however the hormone induced signaling is inhibited. A similar trend of reduced tyrosine phosphorylation of the insulin receptor (IR-β), IRS1 and decreased activation of AKT was observed in Mecp2$^{-/+}$ mice.

Figures 3A, 3B:
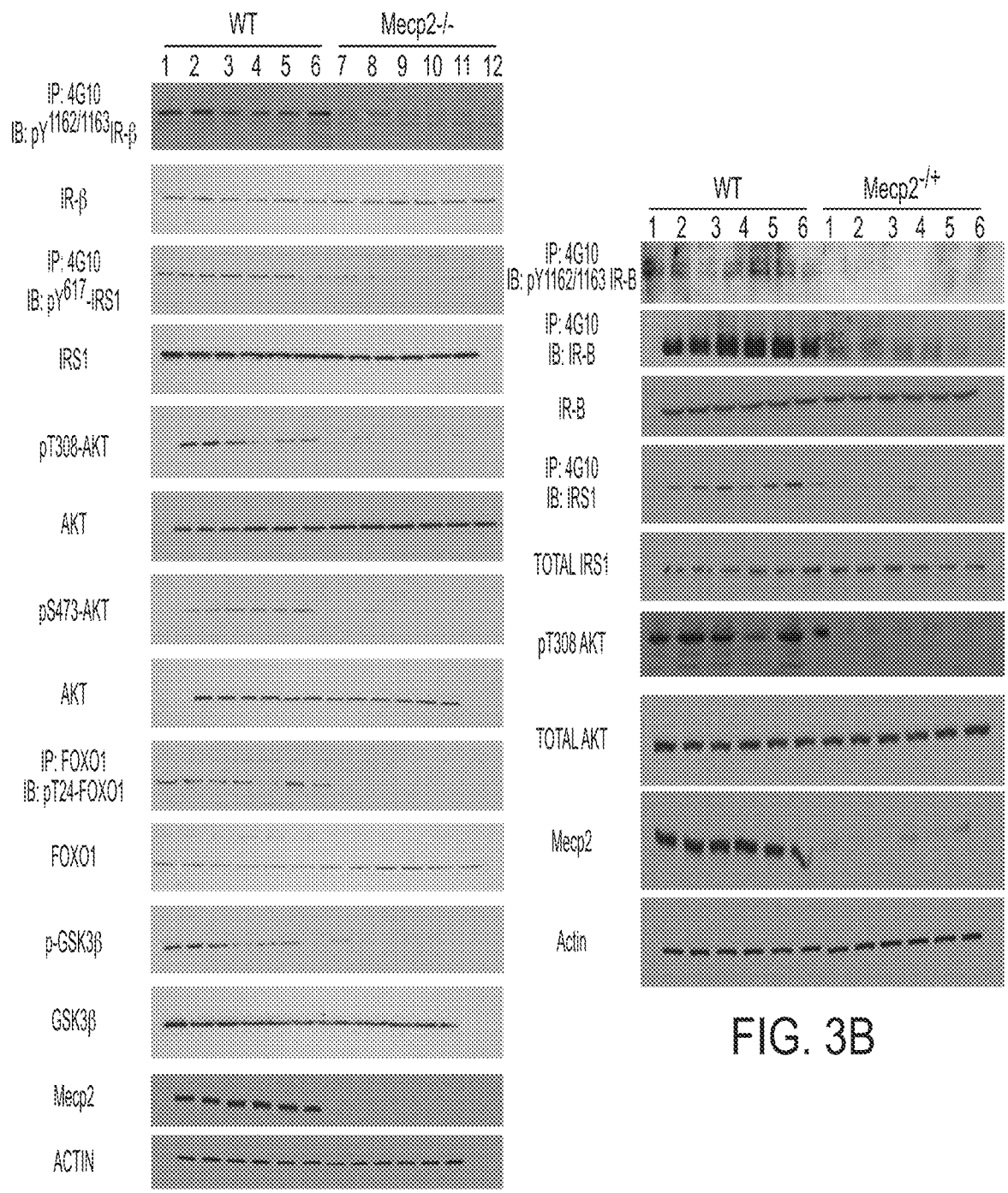
FIGS. 3A and B show impaired insulin signaling observed in Mecp2$^{-/-}$ male mice.

To further examine insulin signaling in the mice, cortex from each control or Mecp2-null mouse was lysed in a RIPA buffer and equal amounts of lysate were immunoblotted using antibodies that recognize various components of the insulin signaling pathway. As shown in FIGS. 3A and B, the insulin signaling was impaired in Mecp2$^{-/-}$ male mice. For example, while the total AKT protein amounts in the control mice and the Mecp2-null mice were about the same, AKT protein phosphorylation in the Mecp2-null mice was significantly reduced or abolished.

Figure 4:
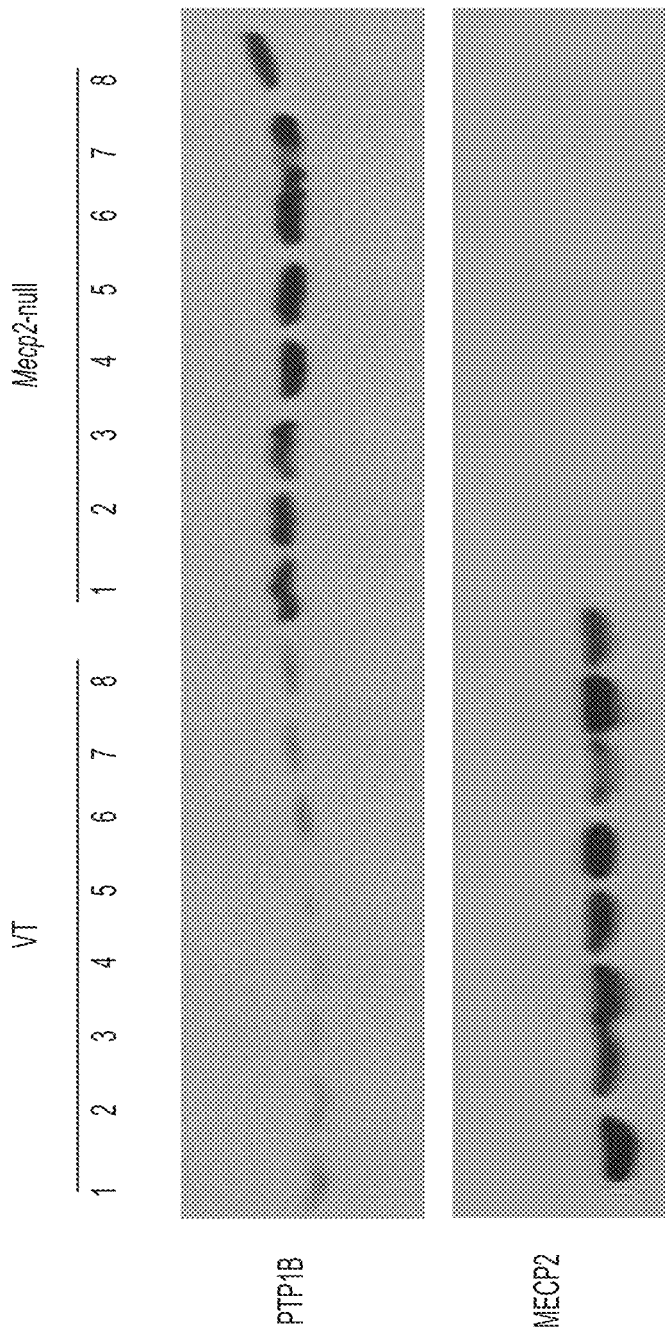
FIG. 4 shows that MECP2 loss was accompanied by increased expression of PTP1B in the cortex.

Similar immunoblot assays were also conducted using anti-PTP1B antibody. It was found that MECP2 loss was accompanied by increased expression of PTP1B in the cortex. See FIG. 4.

Figure 5A:
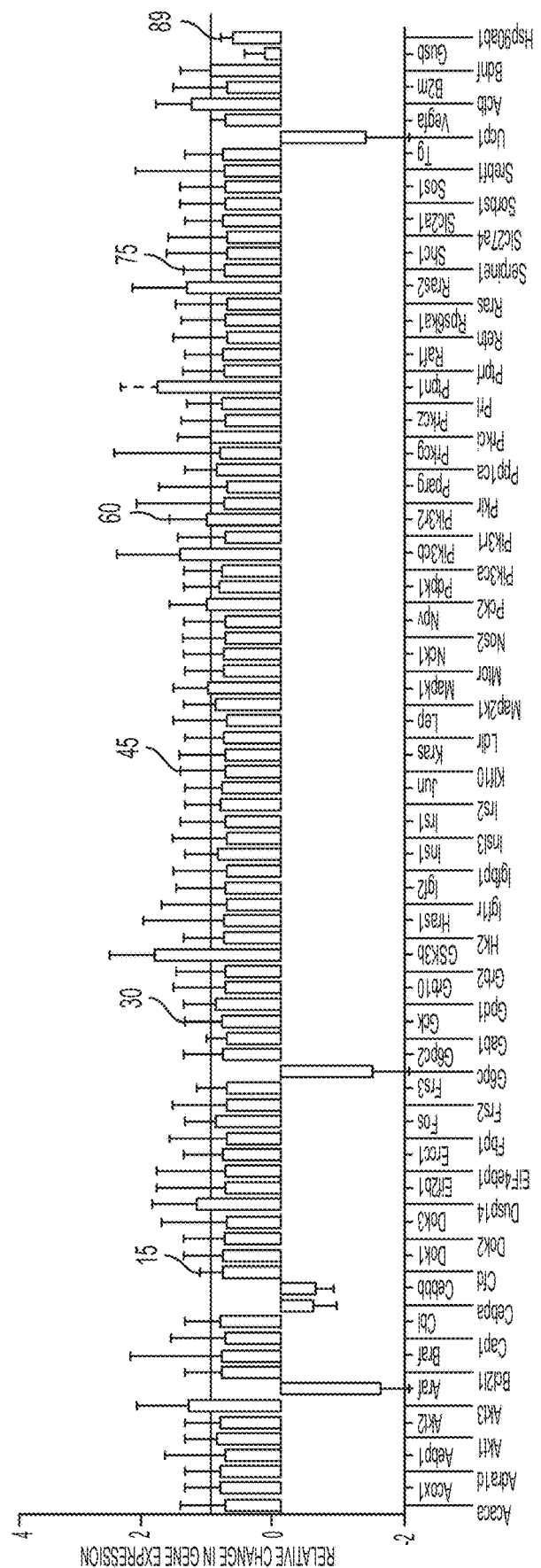
FIGS. 5A-F show that Mecp2 mutant mice express higher levels of PTP1B and that the PTPN1 gene, encoding PTP1B, is a target of MECP2.
Figure 5B:
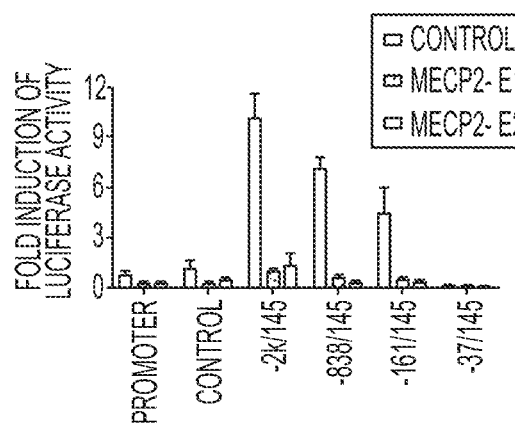
Figure 5C:
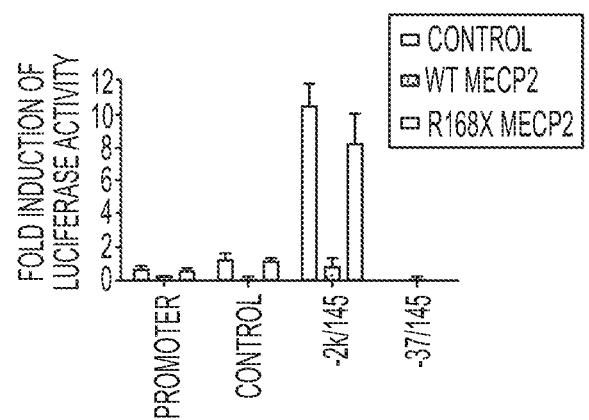

In order to identify genes that are specifically regulated by Mecp2 in the insulin pathway, gene expression analysis in the forebrain region was carried out. Total RNA was isolated from the brain obtained from Mecp2$^{-/y}$ (KO) and their WT littermates. Quantitative PCR of critical genes that are implicated in insulin signaling and glucose metabolism was performed (FIGS. 5A and 5B). Genes whose expression changed by greater than 1.5 fold in Mecp2$^{-/y}$ compared to WT were selected. Attention was focused on the insulin signaling pathway as it was found that 4 genes were significantly upregulated in the KO mice and 5 genes were downregulated. In order to test whether Ptpn1 is a direct target of Mecp2, a series of reporter plasmids in which expression of luciferase is driven by Ptpn1 promoter elements was used. The reporter plasmids containing different lengths of Ptpn1 promoter sequence along with either isoform of Mecp2 (Mecp2-E1 and Mecp2-E2) were expressed. It was observed that both isoforms of Mecp2 were able to suppress the Ptpn1 promoter activity in contrast to cells that expressed just the promoter constructs without Mecp2 (FIG. 5C). Furthermore, unlike wild type MECP2, expression of a clinically relevant loss of function mutant form of the protein, MECP2-R168X, did not suppress PTPN1 promoter activity (FIG. 5C).

Figure 5D:
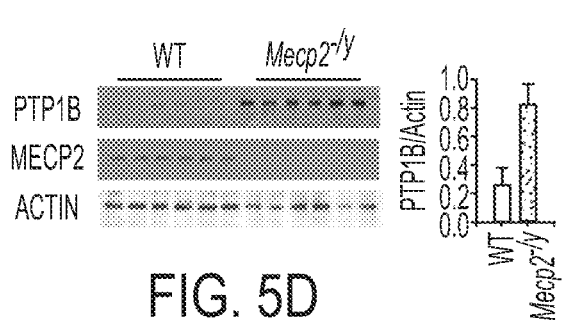
Figure 5E:
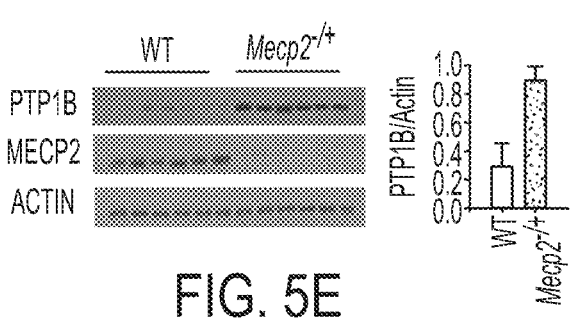
Figure 5F:
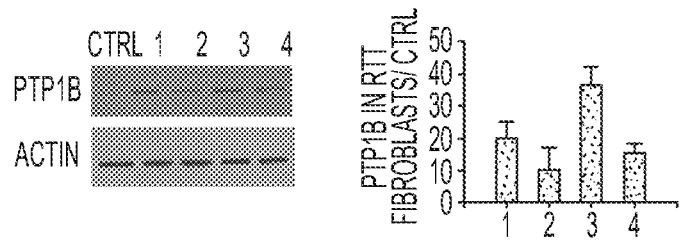

The data indicate that Ptpn1 is a direct target of Mecp2. To further confirm that Mecp2 interacts with the Ptpn1 gene promoter, chromatin immunoprecipitation (ChIP) was carried out. Several genes that have been shown to be involved in insulin signaling were examined to test if Mecp2 specifically targets Ptpn1. Of the genes tested by ChIP analysis, it was found that Mecp2 bound strongly to the promoter region of two proteins, namely Ptpn1 and Eya 2. It was next determined whether the increase in mRNA levels observed by qPCR correlates with the protein level in Mecp2 mutant mice. Equal amounts of lysate from WT and Mecp2$^{-/y}$ brain section were immunoblotted for Ptp1B. It was found that in male mice lacking Mecp2, Ptp1B expression was about 1.5-2 fold higher when compared to the WT counterpart (FIG. 5D). Similarly Ptp1B expression was also higher in female mice lacking Mecp2 (FIG. 5E). The level of Mecp2 expression correlated to Ptp1B levels in Mecp2$^{-/+}$ mice. Ptp1B levels in RTT patient-derived fibroblasts were examined. Consistent with the observation in MECP2 mutant mice, elevated PTP1B protein was observed in fibroblasts derived from Rett syndrome patients (FIG. 5F).

Example 3

Figure 6A:
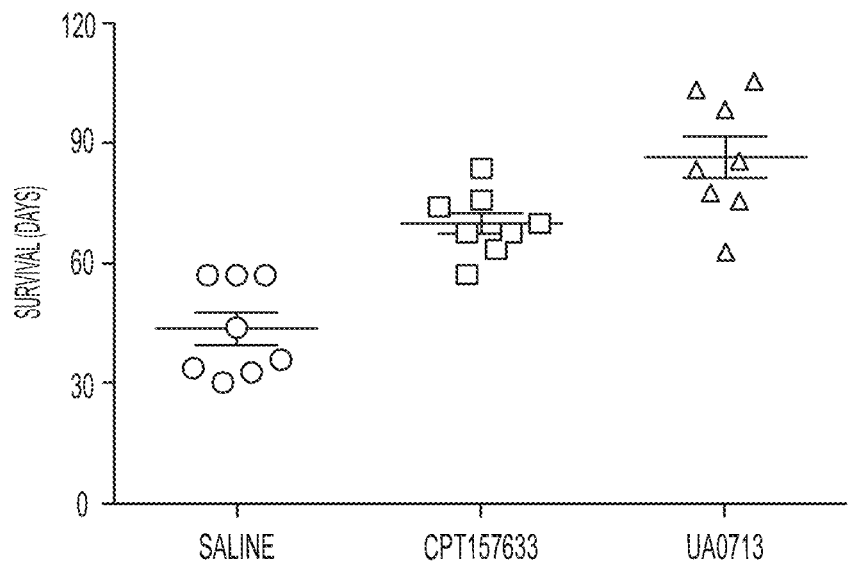
FIGS. 6 A-E show that PTP1B inhibition improved glucose homeostasis and survival in Mecp2 mutant mice.
Figure 6B:
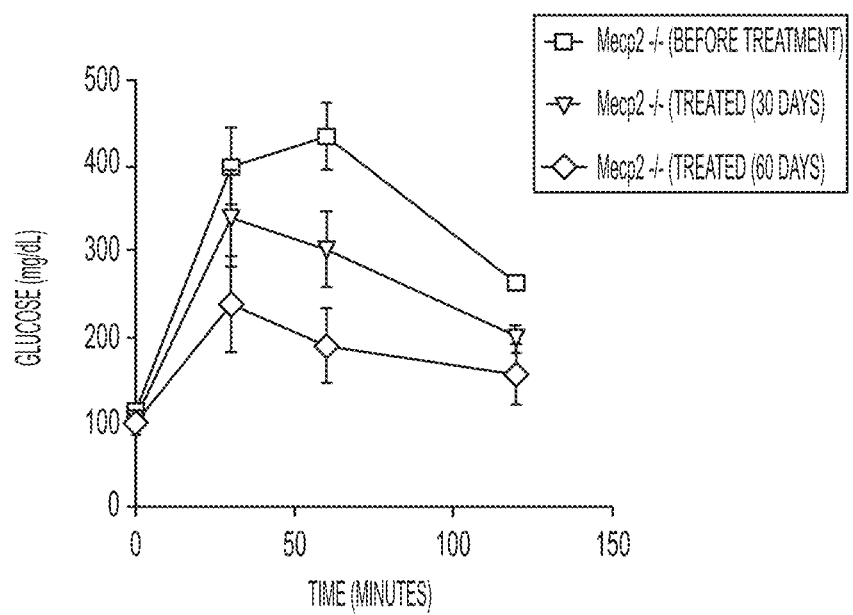
Figure 6C:
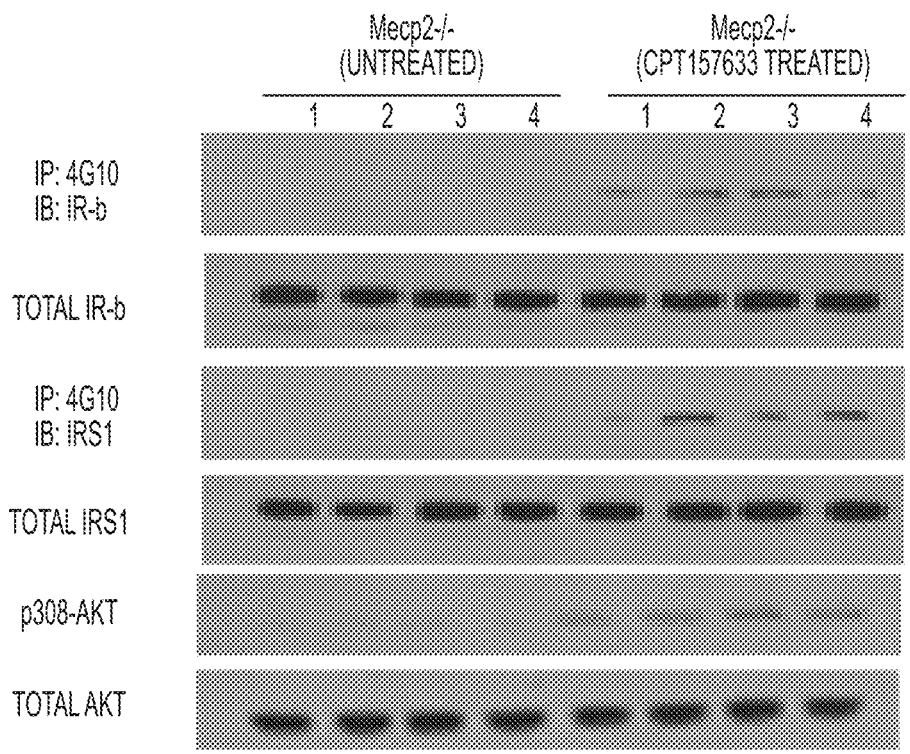
Figure 6D:
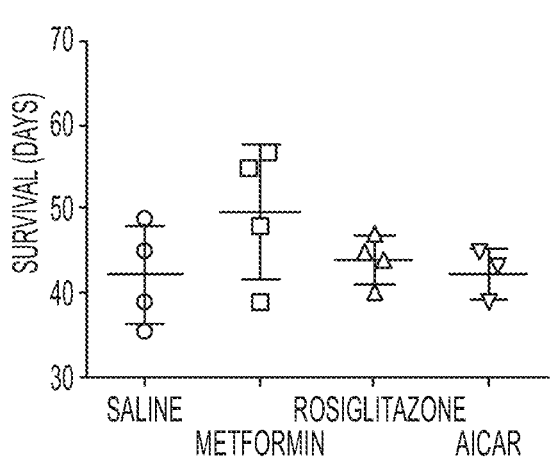
Figure 6E:
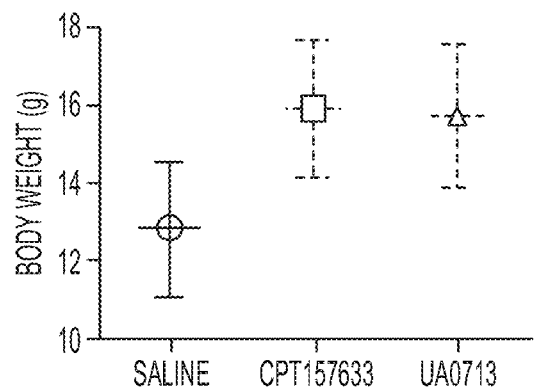

To test if aberrant tyrosine phosphorylation mediated signaling due to enhanced activity of PTP1B could contribute to RTT, pharmacological inhibitors of the phosphatase were used. WT and Mecp2$^{-/y}$ mutant mice were treated with CPT157633 (5 mg/Kg), an active site directed inhibitor of PTP1B, or an allosteric inhibitor, UA0713 (5 mg/Kg). Two weeks after the treatment, serum glucose levels were assessed and it was found that the glucose intolerance that was previously observed was markedly reduced (FIG. 6B). A small increase in body weight in Mecp2$^{-/y}$ mice that were administered CPT157633 when compared to the saline treated mice (FIG. 6E) was observed. There was a significant improvement in circulating levels of insulin and cholesterol levels. The data indicate that PTP1B inhibition caused an overall improvement in metabolism. Further, the treatment increased survival by 2-fold with a median life-span of 75 days for CPT157633 and 95 days for UA0713 treated mice compared to 40 days for saline treated mice (FIG. 6A). To test if the small molecule inhibitors were targeting PTP1B selectively, tyrosine phosphorylation of IR-B and IRS1, two bona fide substrates of the phosphatase, was examined. The inhibitor treatment resulted in enhanced tyrosine phosphorylation of both IR-B and IRS1 as opposed to samples obtained from mice that did not receive CPT157633 (FIG. 6C). In order to understand the role of glucose metabolism in correcting RTT symptoms, three other small molecule inhibitors which have been shown to have anti-diabetic properties were tested, namely metformin, rosiglitazone and AICAR. It was found that none of the three inhibitors were as effective as PTP1B inhibitors (FIG. 6D). The data indicate that PTP1B inhibition is not only regulating insulin signaling and glucose metabolism but also a different signaling pathway, which is critical in reversing the observed phenotype. Further, it was determined whether the inhibitors would have an impact on female Mecp2$^{-/+}$ mice. The effect of inhibitor administration on established glucose homeostasis was studied. Within three weeks of CPT157633 administration, it was found that the glucose intolerance observed with saline untreated female mice was corrected and Mecp2–/+ exhibited a more normal glucose clearance in GTT. Consistently, an improvement in insulin signaling was seen.

Example 4

Figure 13A:
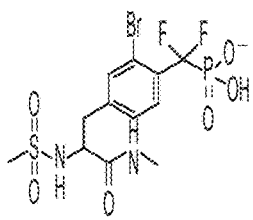
FIGS. 13A-G show the biochemical characterization of PTP1B inhibitor CPT157633.
Figure 13B:
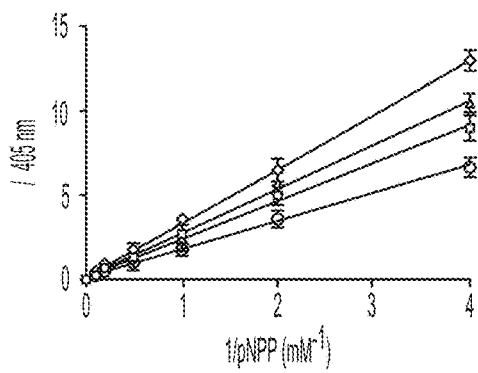
Figure 13C:
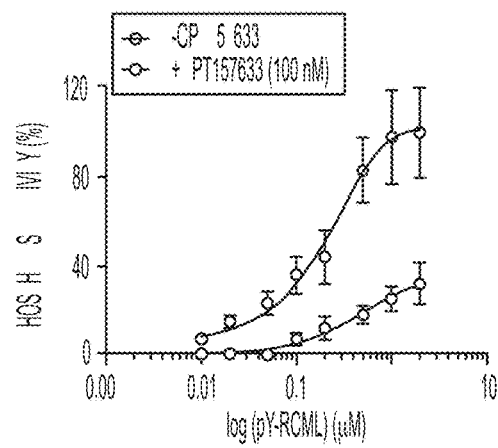
Figure 13D:
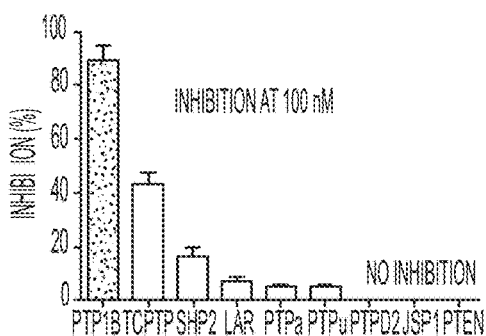
Figure 13E:
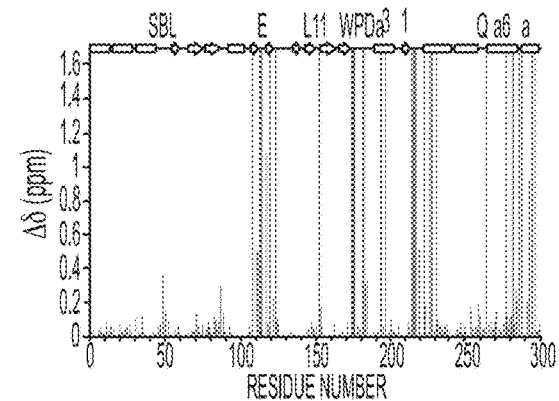
Figure 13F:
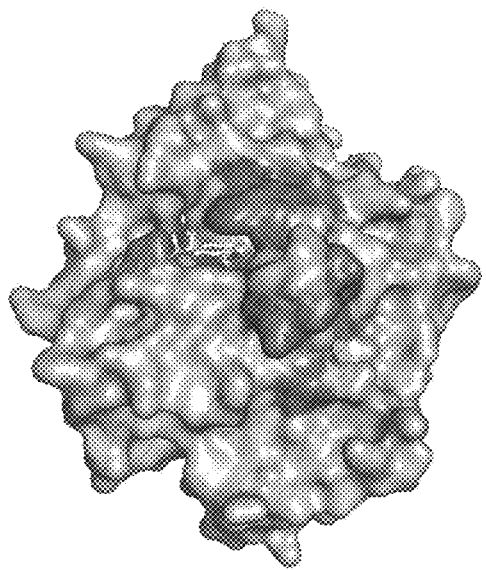
Figure 13G:
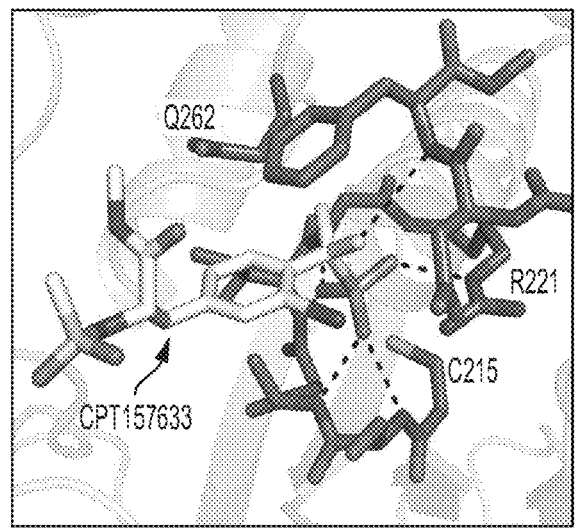

In this example, in order to determine the significance of the elevated PTP1B levels in animal models of Rett syndrome, the effects of small molecule inhibitors of the phosphatase were tested. Using para-Nitro Phenyl Phosphate (pNPP) as substrate, PTP1B inhibition by CPT157633 was studied (FIG. 13A). The compound was found to be a high affinity, competitive inhibitor of the phosphatase (FIG. 13B), with an inhibition constant ($k_i$) of 40 nM. A similar result was obtained using $^{32}$P-labelled RCML as a protein substrate (FIG. 13C). Compared to PTP1B, CPT157633 was markedly less effective against a panel of six PTPs and two dual-specificity phosphatases (FIG. 13D), illustrating specificity in the effects of the inhibitor. To obtain structural insights into the PTP1B-CPT157633 interaction, both biomolecular NMR spectroscopy and X-ray crystallography were used. Residues 1-301 from the catalytic domain of PTP1B were expressed in D$_2$O-based medium and 2D [$^1$H,$^{15}$N] TROSY spectra were recorded in the absence and presence of CPT157633. NMR chemical shift perturbation (CSP) mapping showed that residues surrounding the active site were most affected by CPT157633 binding to the protein (FIGS. 13E, F). This was confirmed by the crystal structure of the PTP1B:CTP157633 complex, which illustrated a non-covalent interaction. Electrostatic interactions made by the compound to critical active site residues are highlighted in FIG. 13G. Together, these data demonstrate that CPT157633 is a selective, reversible, active-site directed inhibitor of PTP1B.

A second inhibitor of PTP1B that exerts its effect on the enzyme by a different mechanism was characterized. Compounds with a triterpene structure, several of which were found to be non-competitive inhibitors of PTP1B, were identified. Of those compounds assayed, UA0713 was found to be the most potent inhibitor of PTP1B. It was observed that UA0713 was a non-competitive inhibitor of PTP1B that inhibited the enzyme with a $K_i$ of 150 nM. It inhibited PTP1B with selectivity compared to a panel of eight phosphatases investigated. This example demonstrates that two high-affinity inhibitors of PTP1B are structurally distinct and inhibit the enzyme by two distinct mechanisms.

Example 5

Figure 7:
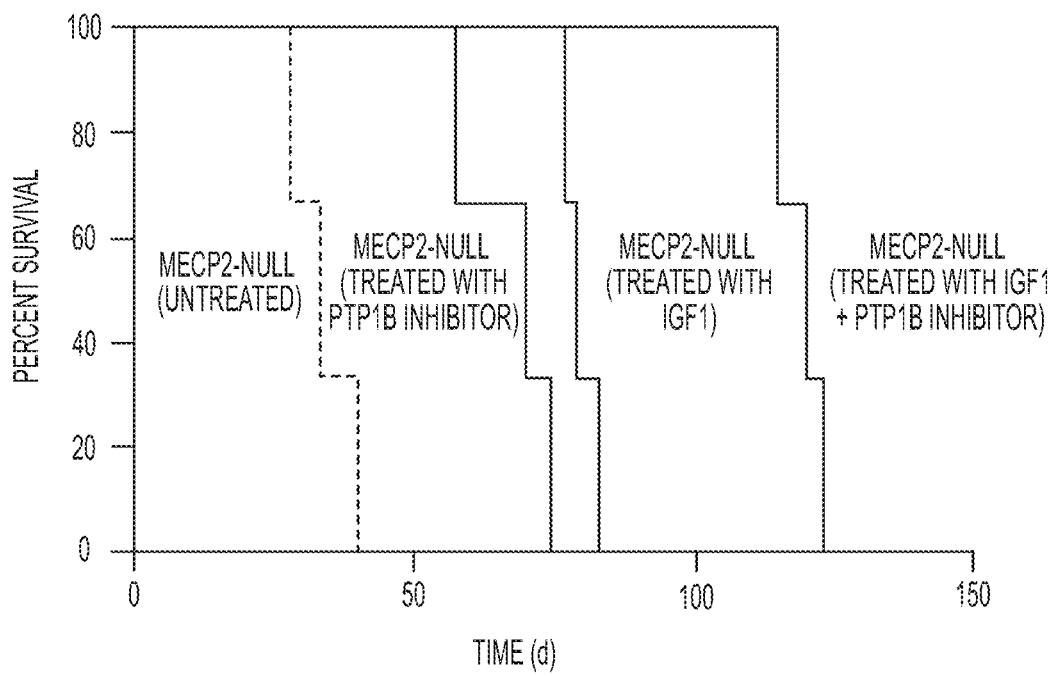
FIG. 7 shows the combinatorial effects of IGF-1 and a PTP1B inhibitor on survival.
Figure 8:
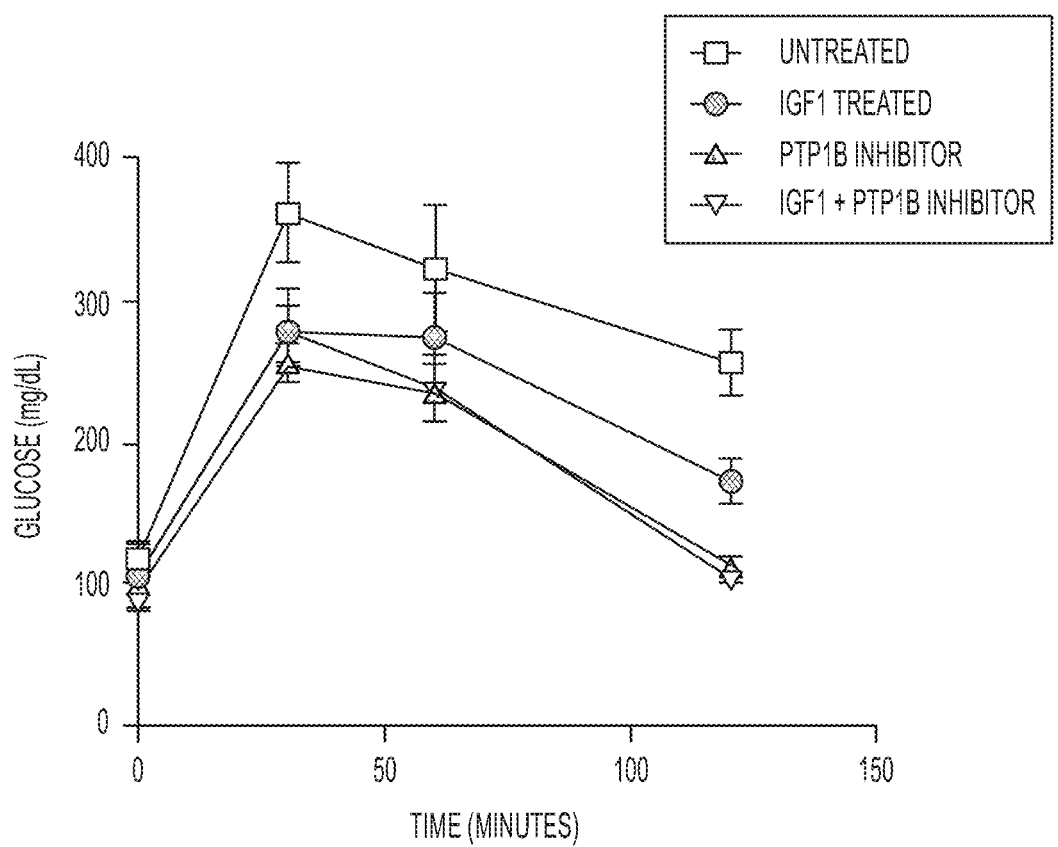
FIG. 8 shows the combinatorial effects of IGF-1 and a PTP1B inhibitor on glucose tolerance.

In this example, assays were carried out to examine synergistic effects between inhibitor CPT157633 and IGF1. Briefly, survival and glucose tolerance tests were conducted on Mecp2$^{-/-}$ male mice and control mice in the same manner described above except that the mice were divided into four groups and received CPT157633 (5 mg/Kg), IGF1 (1 mg/Kg), combination of CPT157633 (5 mg/Kg) and IGF1 (1 mg/Kg), and saline. The results are shown in FIGS. 7 and 8. It was found that IGF-1 and the PTP1B inhibitor when in combination improved the survival and glucose metabolism in a synergistic manner.

The above results indicate that CPT157633 and IGF1 improved survival and insulin signaling in a synergistic manner.

Example 6

Figure 9:
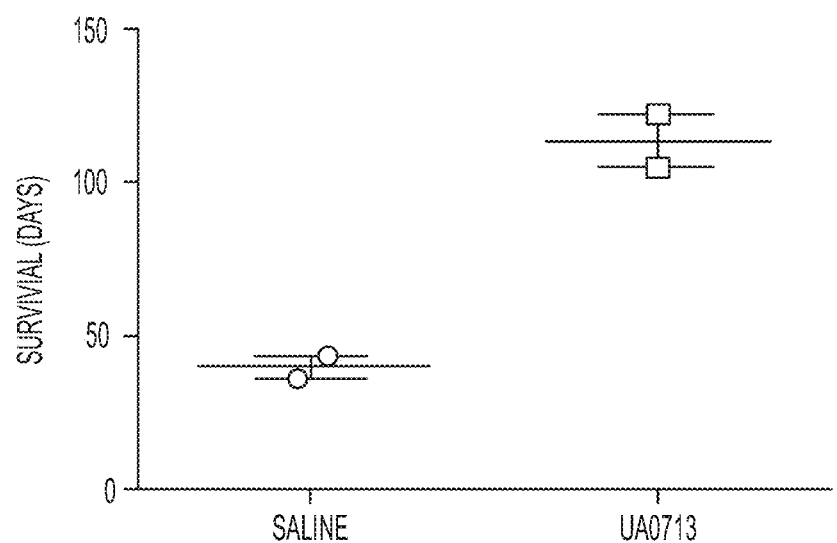
FIG. 9 shows that a structurally and mechanistically distinct inhibitor of PTP1B, UA0713, also improved survival of MECP2-null males.
Figure 10:
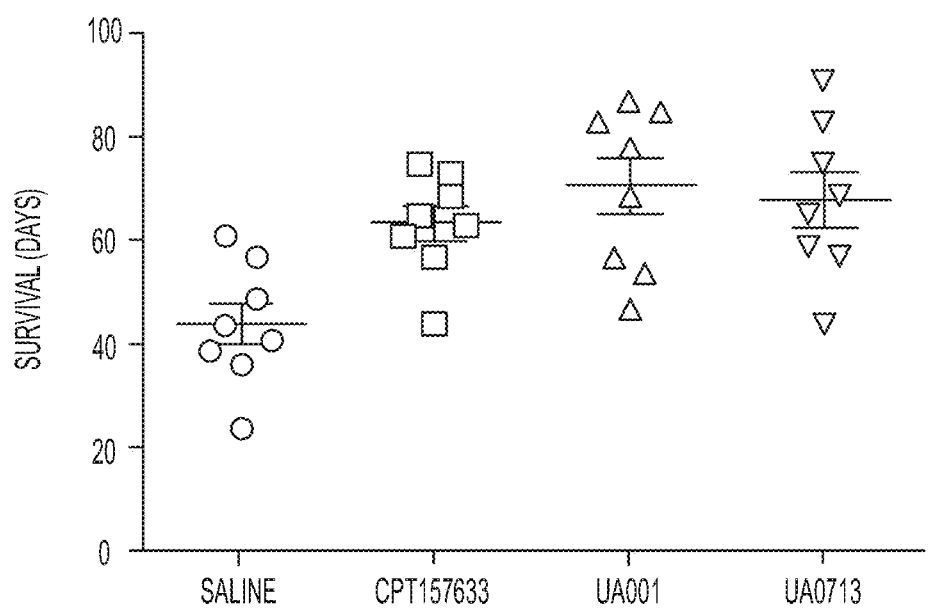
FIG. 10 shows that structurally and mechanistically distinct inhibitors of PTP1B improved survival of MECP2-null male mice.
Figure 11:
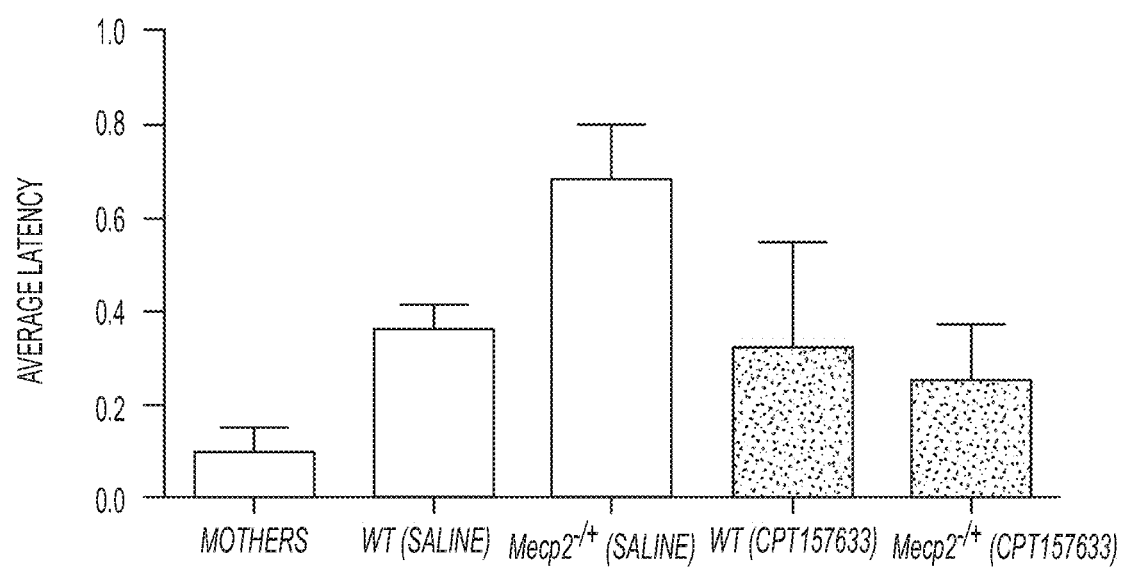
FIG. 11 shows that female Mecp2 heterologous mice displayed enhanced performance in a pup retrieval assay following treatment with PTP1B inhibitor CPT157633.

In this example, additional PTP1B inhibitors were examined for their effects on survival and glucose metabolism in Mecp2$^{-/-}$ male mice. Assays were conducted in the same manner described above using a structurally and mechanistically distinct inhibitor of PTP1B, UA0713 or UA001 (5 mg/kg for each). As shown in FIGS. 9 and 10, both UA0713 and UA001 improved the survival in Mecp2$^{-/-}$ male mice more than CPT157633. The results indicate that PTP1B inhibitors UA001 and UA 0713 can also be used in treating Rett Syndrome.

Example 7

Figure 14A:
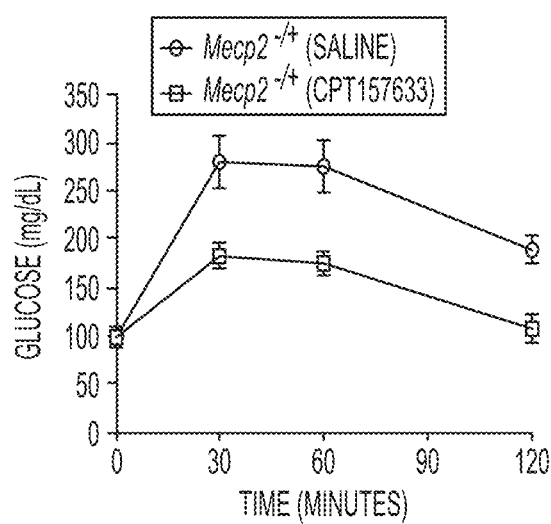
FIGS. 14A-D show that inhibition of PTP1B ameliorates Rett syndrome phenotypes in female mouse models.
Figure 14B:
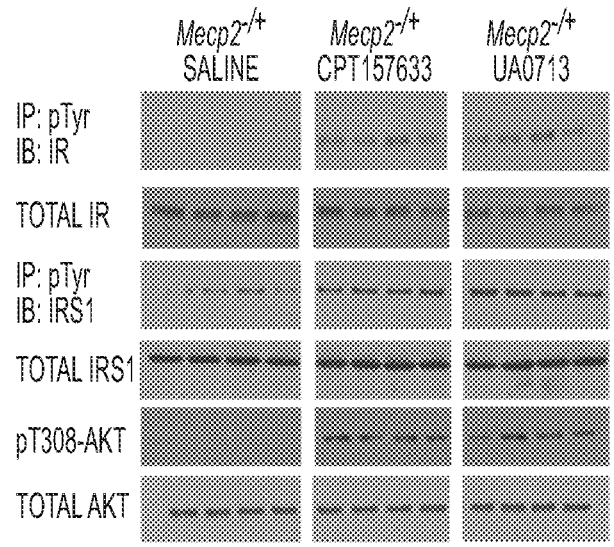

As heterozygous female Mecp2$^{-/+}$ mice are a closer reflection of Rett syndrome in humans than the male mecp2-null mice, the inhibitors of PTP1B were tested in these animals. As a first step, the effects of CPT157633 administration were tested on glucose homeostasis. Consistent with the observation in male mice, it was observed that the glucose intolerance encountered in the saline-treated female Mecp2$^{-/+}$ mice was ameliorated within three weeks of treatment with the inhibitor (FIG. 14A). Consistently, an improvement in insulin signaling was observed (FIG. 14B). Therefore, it was determined whether treatment with CPT157633 also had an impact on neural and behavioral symptoms of Mecp2$^{-/+}$ mice.

Figure 14C:
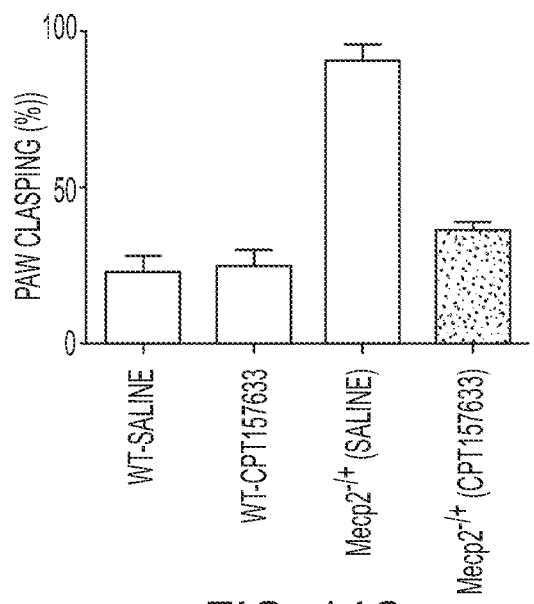

Paw clasping is a classic phenotype consistently observed in Mecp2$^{-/+}$ mice and it is similar to the characteristic hand wringing that is commonly noted in Rett patients. See, Chahrour et al. (2007) Neuron 56: 422-37. When lifted by the tail, wild type mice extended their limbs whereas, in contrast, Mecp2$^{-/+}$ mice clasped their front paws spontaneously for the entire length of time they where monitored, without any significant movement of the paws. Mecp2$^{-/+}$ mice that were administered CPT157633 showed a marked reduction in paw clasping, and extended their paws in a similar manner to wild type animals (FIG. 14C).

Figure 14D:
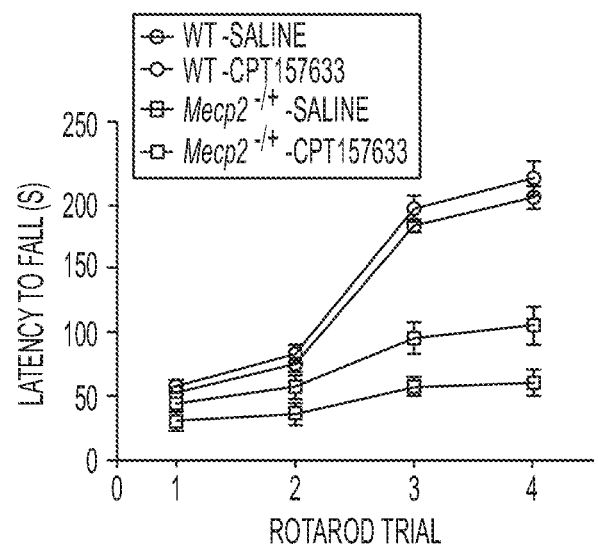

Regression of motor skills is also one of the common symptoms associated with Rett syndrome in patients, which is also observed in Mecp2$^{-/+}$ mice. To test whether inhibition of PTP1B resulted in improved motor skills, saline- and CPT157633-treated WT and Mecp2$^{-/+}$ mice were subjected to a rotarod performance test. In comparison to WT mice, the Mecp2$^{-/+}$ mice showed lower levels of activity on the rotarod. In four successive trials of the WT mice, a dramatic improvement was observed in the time spent on the rotating rod, whereas no improvement was observed with the saline-treated Mecp2$^{-/+}$ mice. However, CPT157633-treated Mecp2$^{-/+}$ mice displayed a significant improvement in performance, although this was a partial restoration and did not achieve wild type levels of performance (FIG. 14D). Furthermore, when CPT157633 treatment was stopped for a week and motor ability was re-tested, it was observed that the improved motor ability that accompanied treatment was lost. This illustrates that the effects of CPT157633 are reversible and prolonged treatment with the compound appears not to have adverse effects in these mice.

Example 8

In this example, behavioral analysis was carried out to examine effects of PTP1B inhibitor CPT157633 on behavior using the pup-retrieval assay.

WT mice when housed with pregnant mothers for a period of three weeks exhibit full maternal behavior when exposed to foster mouse pups, a behavior which is thought to be triggered by pup odor and vocal distress calls. In contrast to the WT mice, the Mecp2$^{-/+}$ mice do not learn the maternal behavior from the mothers, suggesting Mecp2 expression is required for learning and efficient execution of the maternal behavior. Hence, behavior in saline and CPT157633 treated Mecp2$^{-/+}$ mice was studied to understand the effect of PTP1B inhibition on the behavior. One of the maternal behaviors of female mice toward pups is pup retrieval, which is the ability of the mice to bring the pups back into the nest. On the test day four pups were placed into the four corners of the cage and the ability to retrieve all four pups was measured by latency and errors. Only pups brought into the nest completely were counted as retrieved. The assay was performed with the mother (whose pups are used in the study) as a positive control. Scoring was done for latency from 0 to 1, where 0 being quick retrieval and 1 being slow retrieval. The WT mice retrieved pups with an average latency score of 0.3, whereas the Mecp2$^{-/+}$ mice retrieved at an average latency of 0.7, in comparison to the mothers, which retrieved pups with a score of 0.15 (FIG. 3E). The same assay was performed with WT and Mecp2$^{-/+}$ mice that had been treated with CPT157633 for two weeks. CPT157633 treatment caused a slight improvement in the rate at which WT mice retrieved the pups, and there was a significant improvement in the ability of Mecp2$^{-/+}$ mice to retrieve pups with a decreased latency of 0.3 (CPT157633 treated) when compared to the longer latency of 0.7 that was observed with saline treated Mecp2$^{-/+}$ mice (FIG. 13). The data indicate that PTP1B inhibition can rescue the pup retrieval behavior in Mecp2$^{-/+}$ mice. Thus, PTP1B inhibitors can be used to improve learning capacity and neurological functions of Rett Syndrome patients.

Example 9

Figure 12:
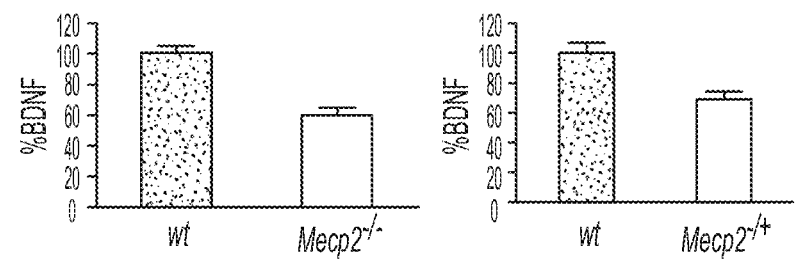
FIG. 12 shows that inhibition of PTP1B led to increased phosphorylation of TrkB and enhanced signaling in response to BDNF.
Figure 12:
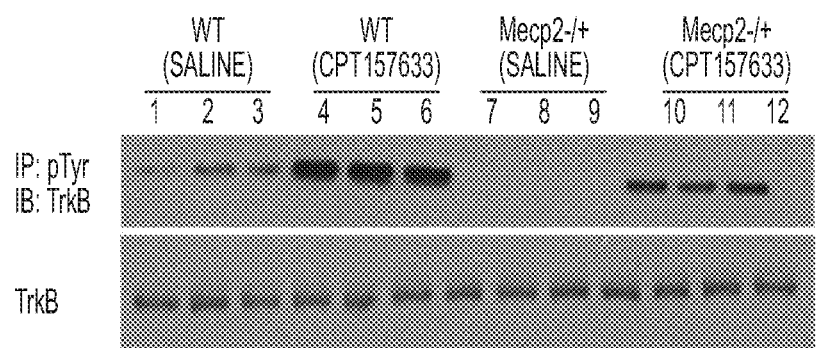
Figure 12:
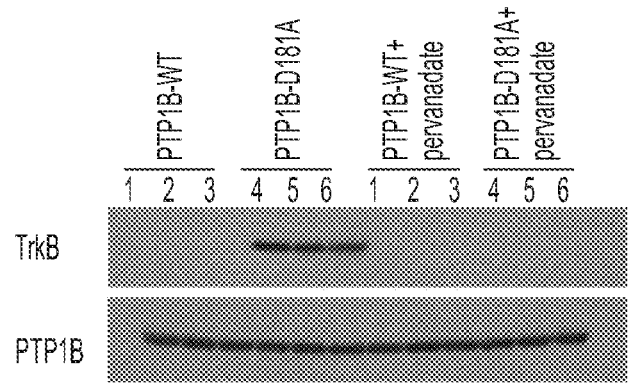

The amount of brain-derived neurotrophic factor (BDNF) in the brain in WT and Mecp2 knockout mice was quantitated. In both Mecp2$^{-/y}$ and Mecp2$^{-/+}$ mice, the level of BDNF was reduced by only about 30% compared to the control WT mice (FIG. 12A). Tyrosine phosphorylation and activation of the BDNF receptor Tropomyosin related kinase B (TrkB) were examined. It was found that saline treated Mecp2$^{-/+}$ mice had reduced TrkB phosphorylation when compared to WT mice. In contrast, CPT157633 treatment resulted in enhanced TrkB phosphorylation in both WT and Mecp2$^{-/+}$ mice (FIG. 12B). The recombinant D181A PTP1B substrate-trapping mutant form of PTP1B was used to investigate the possibility that TrkB is a direct substrate of PTP1B. Brain lysates were generated from saline or PTP1B inhibitor treated mice and incubated equal amount of lysate with WT and D181A mutant form of PTP1B (FIG. 12C). It was observed that D181A PTP1B substrate-trapping mutant, but not the WT enzyme, was able to immunoprecipitate PTP1B (FIG. 12C). Furthermore, treatment of the PTP protein with pervanadate, which promotes oxidation of the active site cysteine and blocks its activity, was incapable of binding to TrkB.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein by reference in their entireties.

What is claimed is:

1. A method for treating Rett Syndrome, comprising administering to a human subject in need thereof an effective amount of a therapeutic agent that is a small molecule inhibitor of protein-tyrosine phosphatase 1B (PTP1B), wherein the effective amount of the inhibitor is selected to inhibit PTP1B as an active site directed inhibitor of PTP1B or an allosteric inhibitor of PTP1B, provided that the inhibitor is not carbenoxolone.

2. The method of claim 1, further comprising testing the subject for a mutation in a gene encoding methyl CpG-binding protein 2 (MECP2).

3. The method of claim 2, wherein the testing comprises nucleic acid detection and the nucleic acid detection is an assay selected from the group consisting of polymerase chain reaction (PCR), reverse transcription polymerase chain reaction (RT-PCR), quantitative PCR, nucleic acid sequencing, nucleic acid microarray analysis, and fluorescence in situ hybridization.

4. The method of claim 2 wherein the testing comprises nucleic acid sequencing of one or more of the coding regions and exon/intron boundaries of the MECP2 gene.

5. The method of claim 1 wherein the small molecule inhibitor of PTP1B is ursolic acid (UA001),

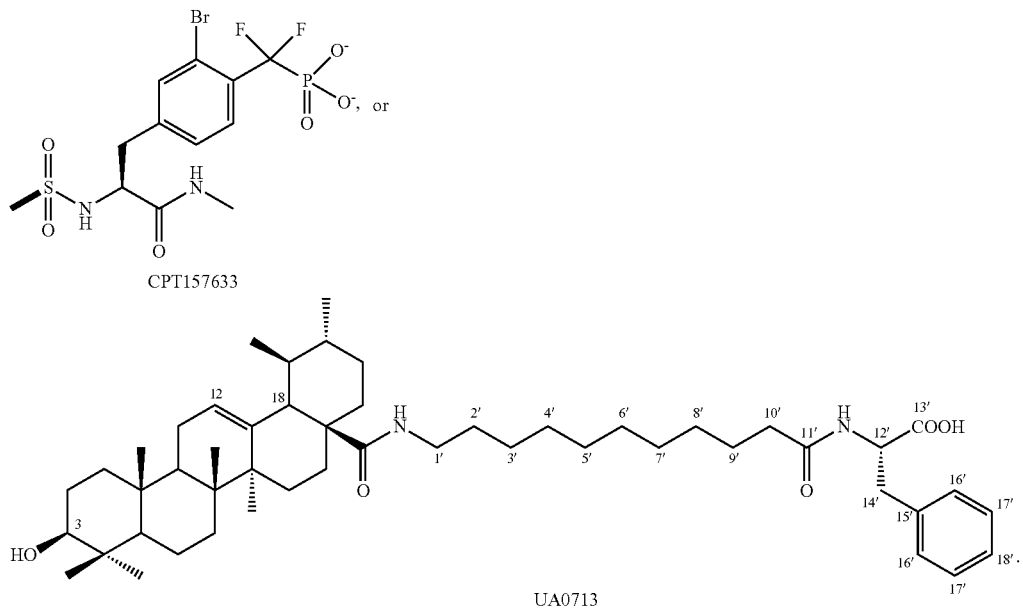

6. The method of claim 1 wherein the small molecule inhibitor of PTP1B is selected from the group consisting of 18β-glycyrrhetinic acid, celastrol, pristimerin, maslinic acid, limonin, arjunolic acid, hederagenin, betulin, lupeol, uveol, ursolic acid, betulinic acid, corosolic acid, oleanolic acid, boswellic acid, friedelin, momordicin, momordicinin, moronic acid, amyrin, bevirimat, hopane, oleanane, panaxatriol, taraxerol, momordicilin, and yamogenin.

7. The method of claim 1, wherein the inhibitor is the active site directed inhibitor of PTP1B.

8. The method of claim 1, wherein the inhibitor is the allosteric inhibitor of PTP1B.

* * * * *